(12) United States Patent
McKean et al.

(10) Patent No.: US 12,740,987 B2
(45) Date of Patent: Sep. 22, 2026

(54) SOLUBLE PHARMACEUTICAL COMPOSITIONS COMPRISING SALTS OF DISUBSTITUTED 1, 2, 4-TRIAZINE COMPOUND

(71) Applicants: Mineralys Therapeutics, Inc., San Fransisco, CA (US); Tanabe Pharma Corporation, Osaka (JP)

(72) Inventors: Robert McKean, Radnor, PA (US); Roch Thibert, Radnor, PA (US); Elizabeth Vadas, Radnor, PA (US); Yoshinori Ohashi, Osaka (JP); Fuminori Ozaki, Osaka (JP); Hiroki Ohshima, Osaka (JP); Hiroomi Nagata, Osaka (JP)

(73) Assignees: MINERALYS THERAPEUTICS, INC., San Fransisco, CA (US); TANABE PHARMA CORPORATION, Osaka (JP)

( * ) Notice: Subject to any disclaimer, the term of this patent is extended or adjusted under 35 U.S.C. 154(b) by 402 days.

(21) Appl. No.: 18/580,999

(22) PCT Filed: Jul. 20, 2022

(86) PCT No.: PCT/IB2022/056709

§ 371 (c)(1),
(2) Date: Jan. 19, 2024

(87) PCT Pub. No.: WO2023/002407

PCT Pub. Date: Jan. 26, 2023

(65) Prior Publication Data

US 2024/0366616 A1 Nov. 7, 2024

Related U.S. Application Data

(60) Provisional application No. 63/223,711, filed on Jul. 20, 2021.

(51) Int. Cl.

| | |
|---|---|
| ***A61K 31/53*** | (2006.01) |
| ***A61K 9/20*** | (2006.01) |
| ***A61K 9/28*** | (2006.01) |
| ***C12Q 1/00*** | (2006.01) |

(52) U.S. Cl.

CPC ............ *A61K 31/53* (2013.01); *A61K 9/2013* (2013.01); *A61K 9/2018* (2013.01); *A61K 9/2027* (2013.01); *A61K 9/2054* (2013.01); *A61K 9/2059* (2013.01); *A61K 9/284* (2013.01)

(58) Field of Classification Search

CPC ............ A61K 31/53; A61P 9/12; C12Q 1/001
USPC .......................................... 514/242; 435/184
See application file for complete search history.

(56) References Cited

U.S. PATENT DOCUMENTS

| | | | |
|---|---|---|---|
| 10,029,993 | B2 | 7/2018 | Ushirogochi |
| 10,329,263 | B2 | 6/2019 | Ushirogochi |
| 10,717,731 | B2 | 7/2020 | Sakakibara |
| 11,339,135 | B2 | 5/2022 | Yamagami |
| 2013/0296309 | A1 | 11/2013 | Chamoin |
| 2014/0323468 | A1 | 10/2014 | Balestra |
| 2015/0094308 | A1 | 4/2015 | Follman |
| 2015/0209285 | A1 | 7/2015 | Van Speybroek et al. |
| 2017/0044115 | A1 | 2/2017 | Ushirogochi et al. |
| 2023/0365513 | A1 | 11/2023 | Yamagami |

FOREIGN PATENT DOCUMENTS

| | | | |
|---|---|---|---|
| WO | WO 2022/093714 | A1 | 5/2022 |
| WO | WO 2023/002407 | A2 | 1/2023 |
| WO | WO 2023/139506 | A1 | 7/2023 |

OTHER PUBLICATIONS

International Preliminary Report on Patentability issued Jan. 18, 2024, in connection with PCT International Application No. PCT/IB2022/056709.

Patel "Rational Design of Pharmaceutical Salt Formulations by Understanding the Mechanism of Disproportionation" Purdue University, 2018, p. 1-165.

USP-NF "The Dissolution Procedure; Development and Validation" May 14, 2021, p. 1-23.

Li et al., "Lubricants in Pharmaceutical Solid Dosage Forms" Lubricants. Feb. 25, 2014 p. 21-43.

International Search Report issued Jan. 12, 2023 in connection with PCT International Application No. PCT/IB2022/056709.

Written Opinion of the International Searching Authority issued Jan. 12, 2023 in connection with PCT International Application No. PCT/IB2022/056709.

Apr. 16, 2025 Extended European Search Report issued in connection with European Patent Application No. 22845541.6.

(Continued)

*Primary Examiner* — Charanjit Aulakh
(74) *Attorney, Agent, or Firm* — Gary J. Gershik

(57) ABSTRACT

Disclosed are pharmaceutical compositions comprising a salt of a compound having the formula:

3-[4-[[trans-4-(acetoamino)cyclohexyl]carbamoylmethyl]piperazin-1-yl]-5-(p-tolyl)-1,2,4-triazine and one or more excipients, wherein the pharmaceutical composition avoids inducing disproportionation of the salt of the compound.

21 Claims, 14 Drawing Sheets

(56) References Cited

OTHER PUBLICATIONS

Christopher T. John et al: "Formulating Weakly Basic HCI Salts: Relative Ability of Common Excipients to Induce Disproportionation and the Unique Deleterious Effects of Magnesium Stearate", Pharmaceutical Research, vol. 30, No. 6, Mar. 20, 2013 (Mar. 20, 2013) , pp. 1628-1641, XP055756244, Berlin/Heidelberg ISSN: 0724-8741, DOI: 10.1007/s11095-013-1002-y.

Nov. 7, 2025 Response to Apr. 16, 2025 Extended European Search Report filed in connection with European Patent Application No. 22845541.6.

Feb. 6, 2026 Communication Pursuant to Article 94(3) EPC issued in connection with European Patent Application No. 22845541.6.

Jun. 6, 2026 Response to Feb. 6, 2026 Communication Pursuant to Article 94(3) EPC filed in connection with European Patent Application No. 22845541.6.

Laffin, Luke J., et al. "Lorundrostat efficacy and safety in patients with uncontrolled hypertension." New England Journal of Medicine 392.18 (2025): 1813-1823.

Supplementary Appendix of Laffin, Luke J., et al. "Lorundrostat efficacy and safety in patients with uncontrolled hypertension." New England Journal of Medicine 392.18 (2025): 1813-1823.

Laffin, Luke J., et al. "Aldosterone synthase inhibition with lorundrostat for uncontrolled hypertension: the target-HTN randomized clinical trial." Jama 330.12 (2023): 1140-1150.

Shimizu, Hidetoshi, et al. "First-in-human study evaluating safety, pharmacokinetics, and pharmacodynamics of lorundrostat, a novel and highly selective aldosterone synthase inhibitor." Clinical and Translational Science 17.8 (2024): e70000.

Saxena, Manish, et al. "Lorundrostat in participants with uncontrolled hypertension and treatment-resistant hypertension: the Launch-HTN randomized clinical trial." Jama 334.5 (2025): 409-418.

Ogawa, K., et al., "First-In-Human Study of lorundrostat, a Potent and Highly Selective Aldosterone Synthase Inhibitor," Poster presented at: American College of Cardiology Scientific Session, New Orleans, Louisiana, Mar. 4-6, 2023.

Rodman, D., et al. "Lorundrostat for Treatment of Obesity-Related, Aldosterone-Dependent Hypertension—an Endotype-Specific, Targeted Approach to the Treatment of Uncontrolled Hypertension," Poster presented at: the American Heart Association Scientific Sessions, Nov. 11-13, 2023, Philadelphia, PA.

Melting point
- Stearic acid: 55°C–70°C
- Sucrose fatty acid ester: 51°C–70°C
- Hydrogenated oil: 65°C–70°C

Figure 5: XRPD diffractograms of final blend and uncoated tablet for DC lot 1.
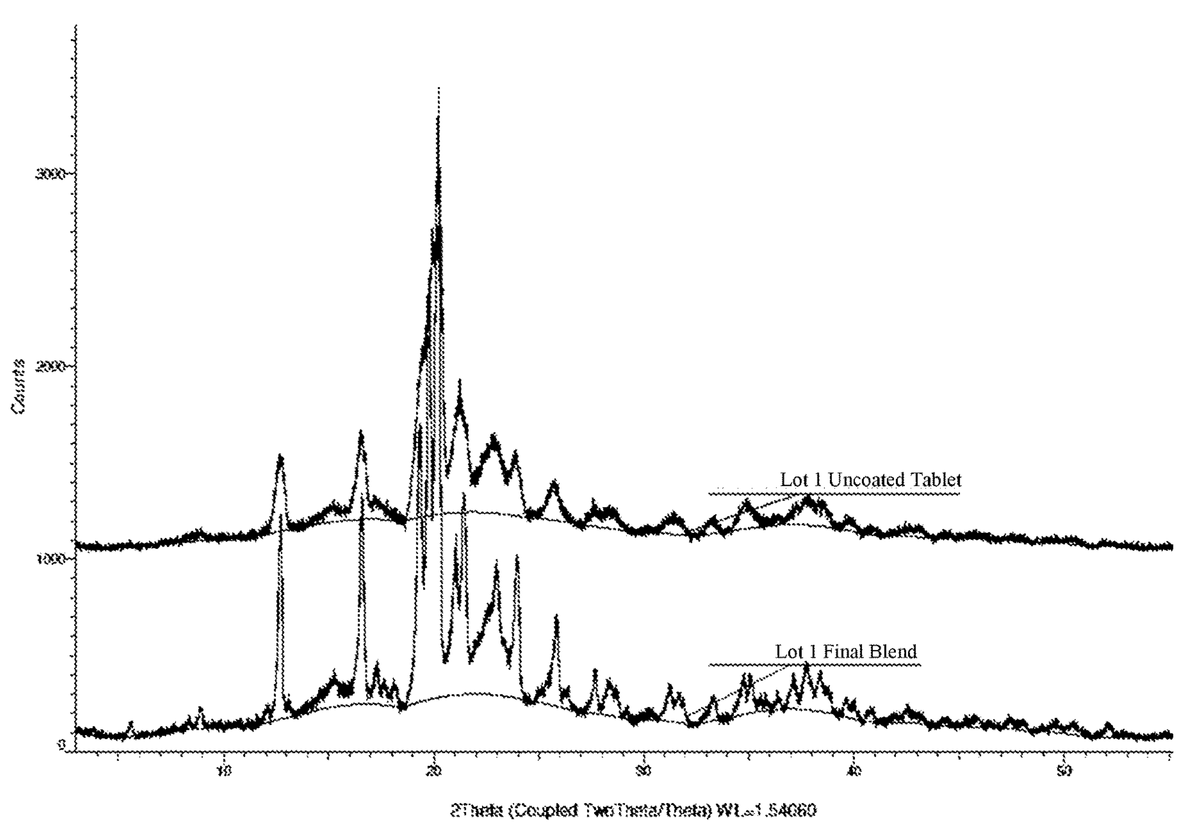

Figure 6: XRPD diffractograms of final blend and uncoated tablet for DC lot 4.
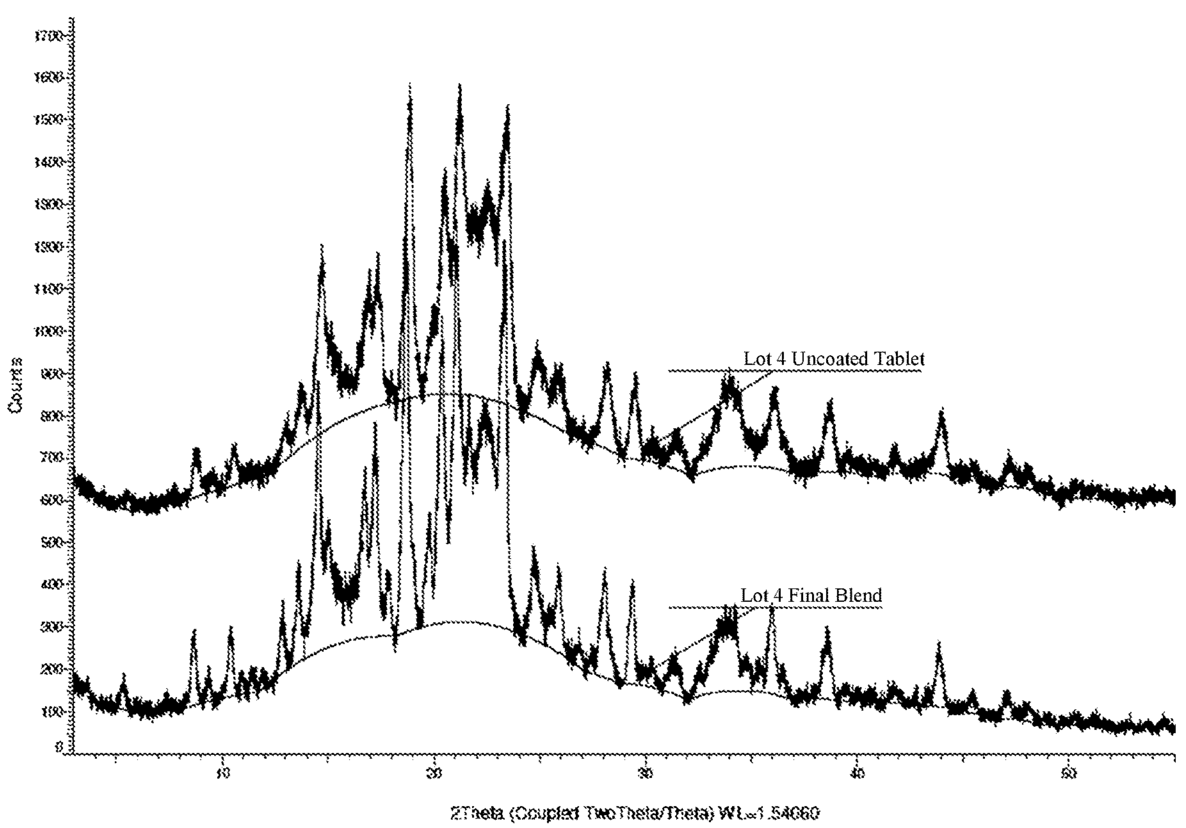

Figure 7: XRPD diffractograms of final blend and uncoated tablet for DC lot 5.
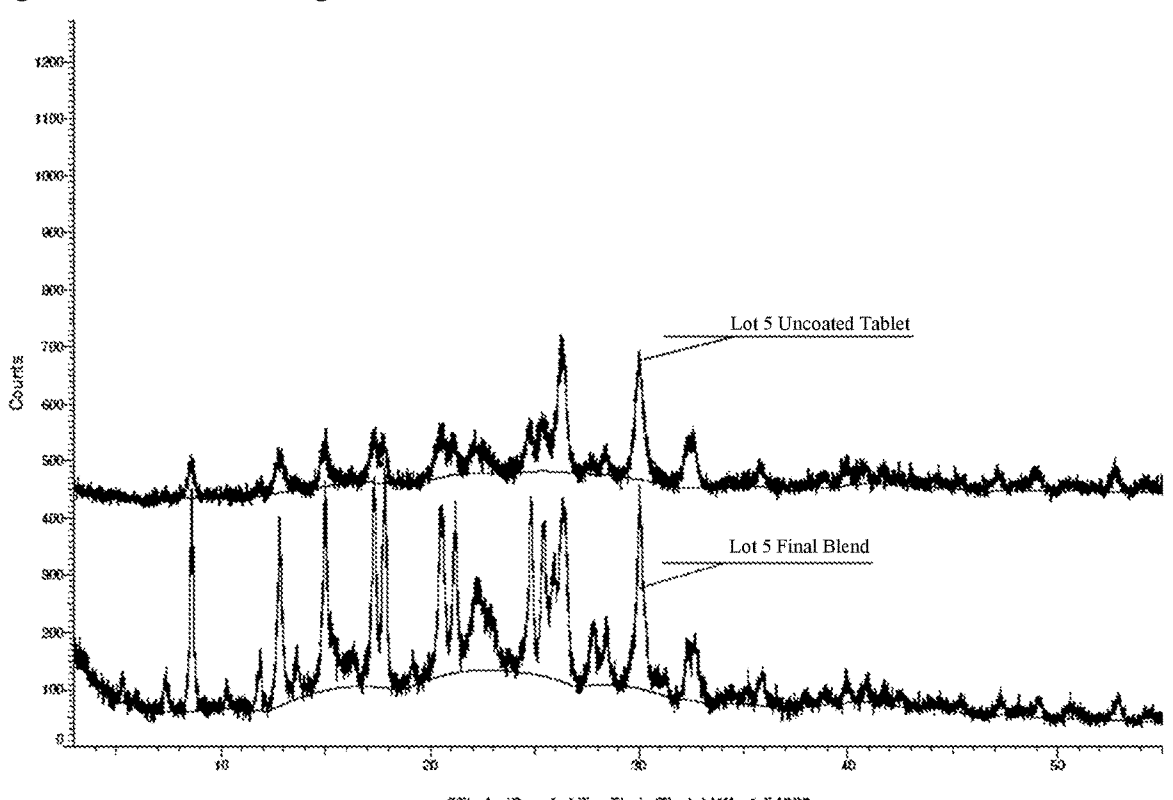

Figure 8: XRPD diffractograms of at various steps of HSWG manufacturing process for lot 6.
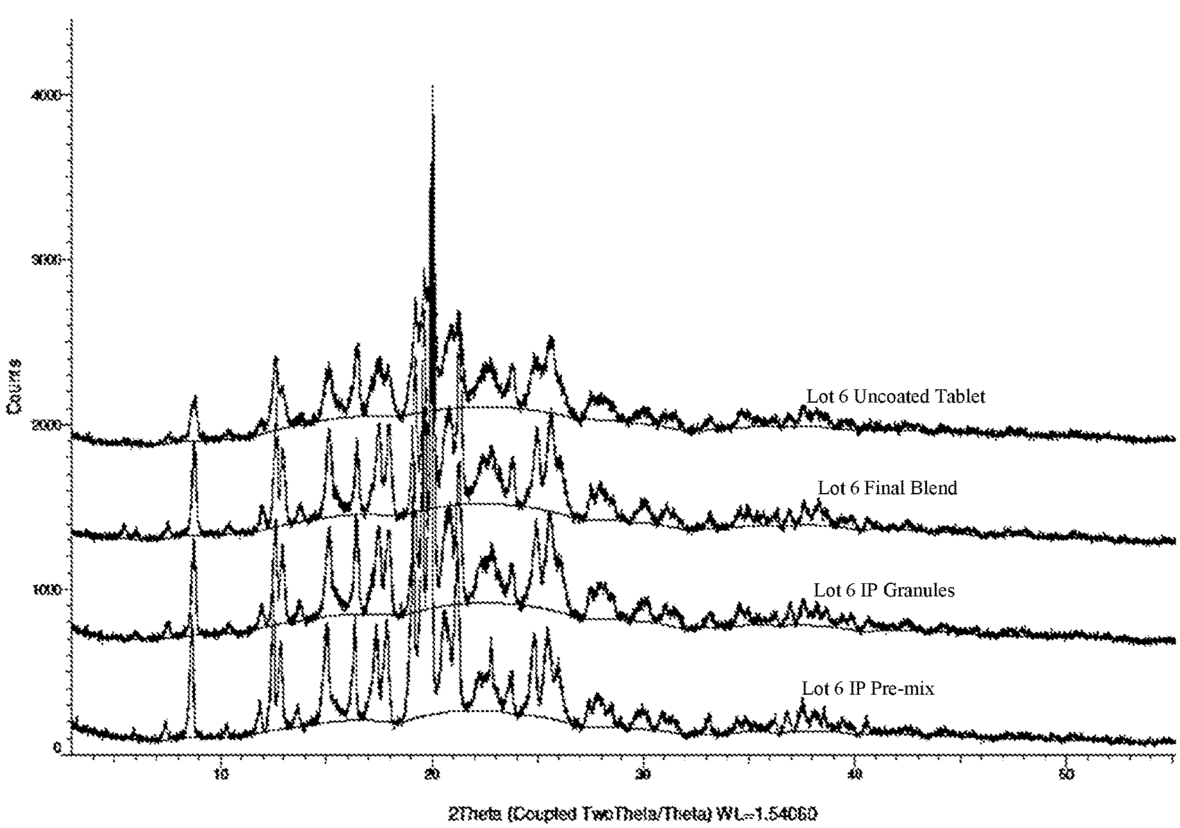

Figure 9: XRPD diffractograms of lot 11 final blend, uncoated tablet, and film coated tablet.
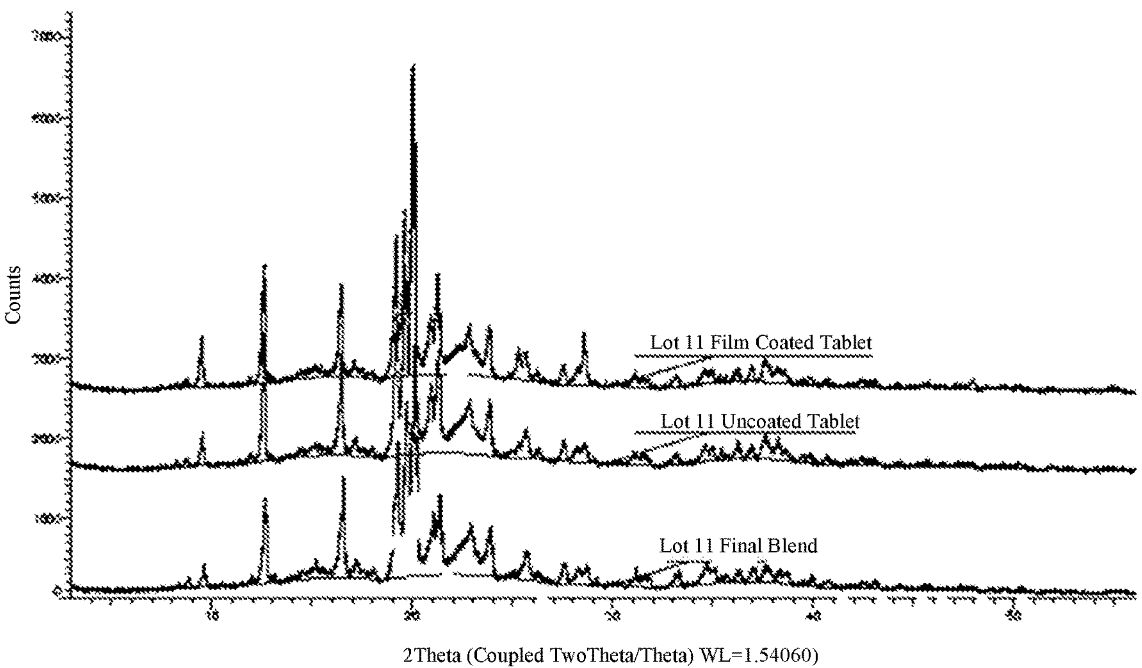
Figure 10: XRPD diffractograms of lot 13 final blend, uncoated tablet, and film coated tablet.
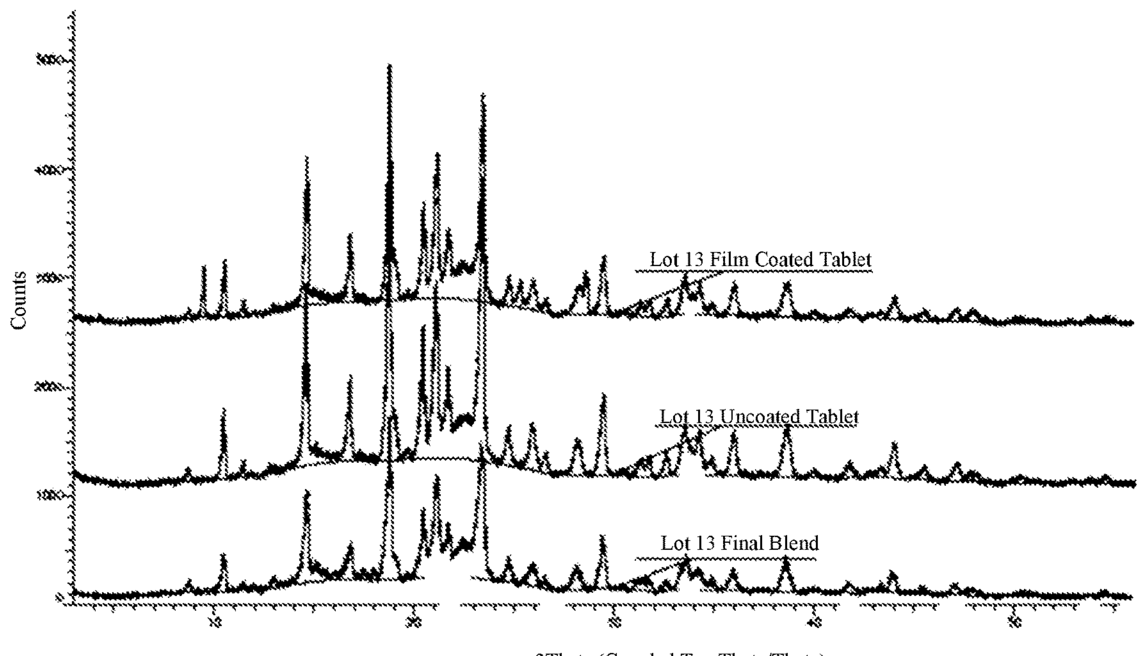

Figure 11: XRPD diffractograms of lot 15 final blend, uncoated tablet, and film coated tablet.
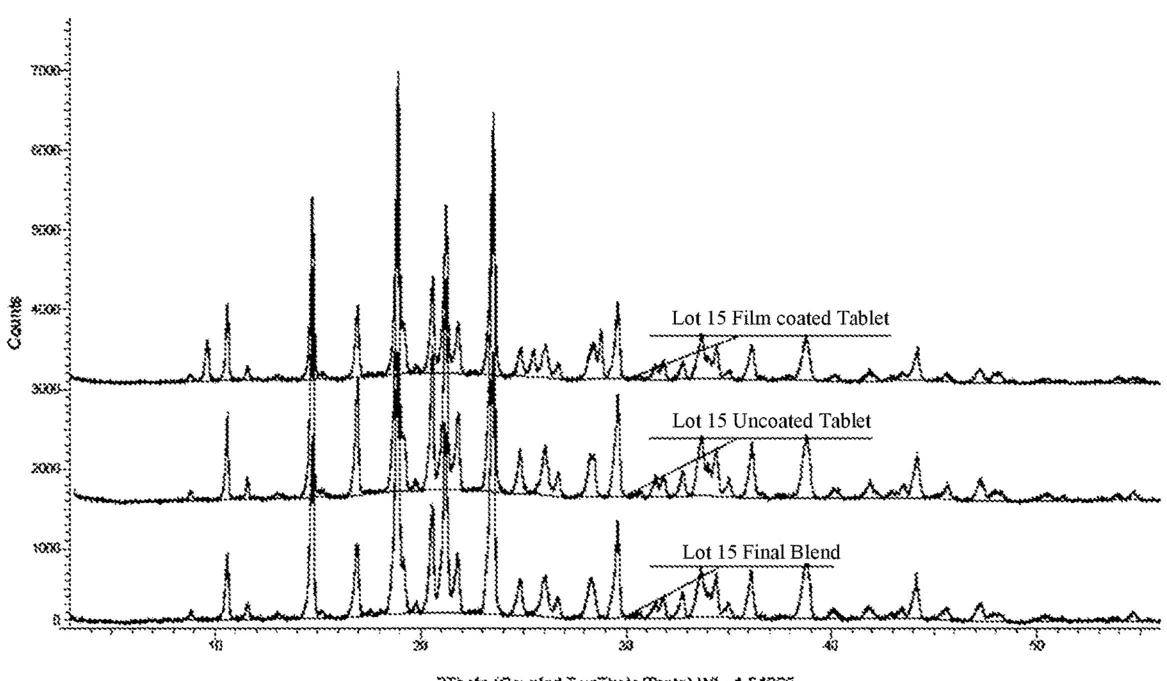

Figure 12: XRPD diffractograms of 17 final blend, uncoated tablet (Trials #1 & #2), and film coated tablet (Trials #2).
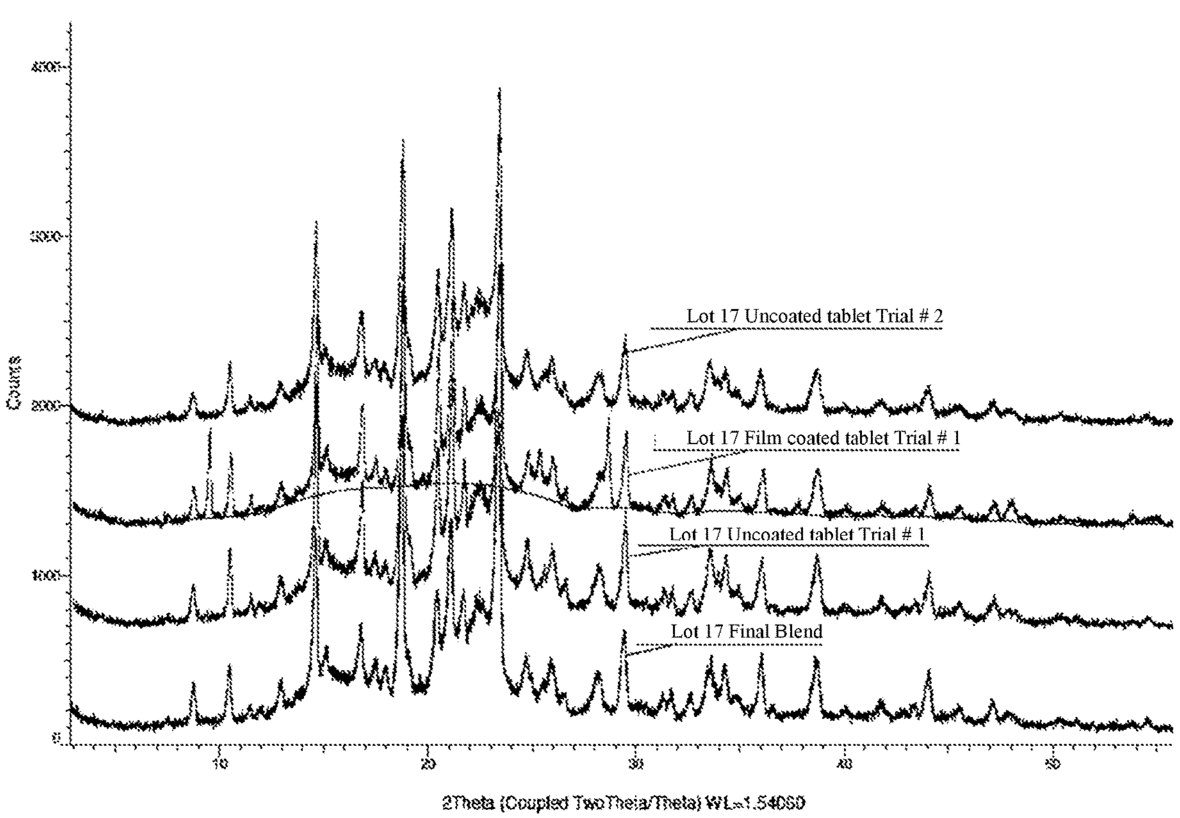

Figure 13: XRPD diffractograms of 18 final blend, uncoated tablet (Trials #1/#2 & #3), and film coated tablet (Trials #2).
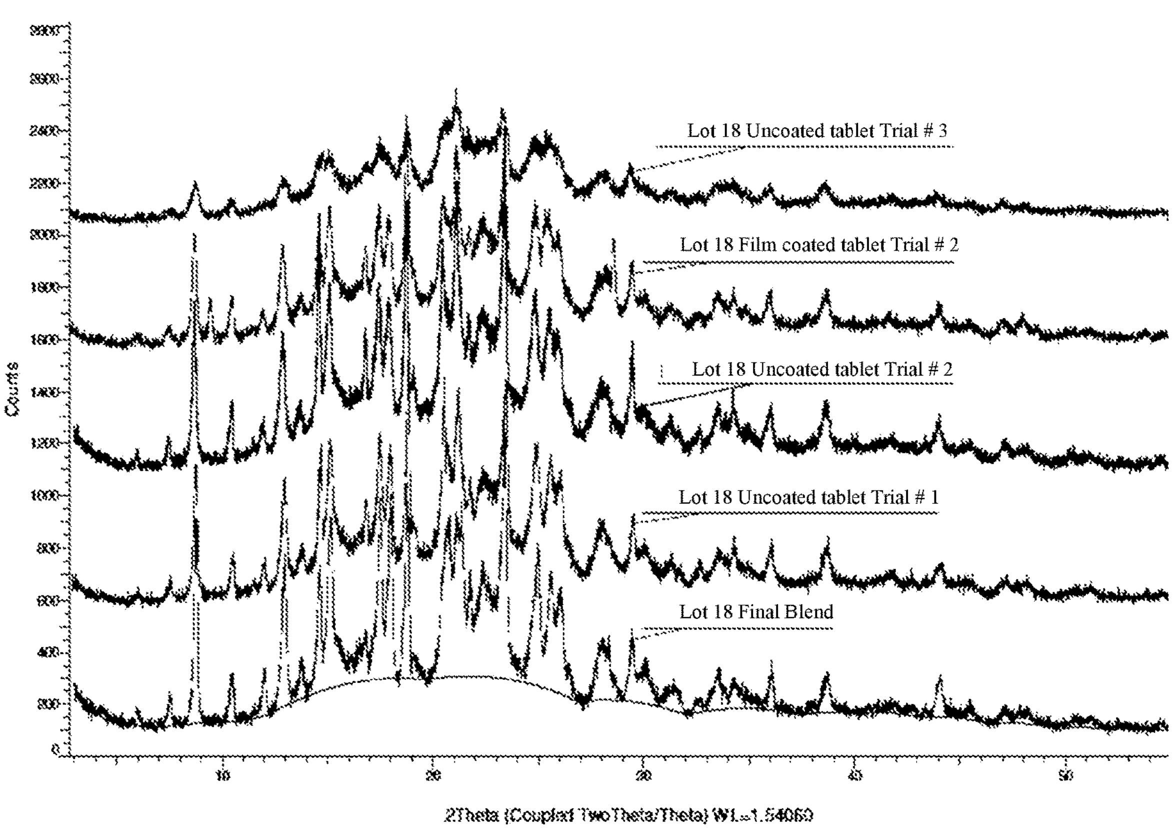

Figure 14: Summary of Analytical data for prototype formulations

| Lot | | 1 | | 4 | | 5 | | 6 | |
|---|---|---|---|---|---|---|---|---|---|
| Dose strength (mg) | | 12.5 | | 25 | | 100 | | 100 | |
| Description (Visual) | | White, round biconvex tablet | | White, round biconvex tablet | | White, round biconvex tablet | | White, round biconvex tablet | |
| Assay | %LC | 96.7 | | 98.8 | | 98.8 | | 100.1 | |
| | Method revision | R&D 01 | | R&D 01 | | R&D 01 | | R&D 01 | |
| Related Substances | Total Impurities: | No impurity ≥ 0.05% | | No impurity ≥ 0.05% | | No impurity ≥ 0.05% | | No impurity ≥ 0.05% | |
| | Method revision | R&D 01 | | R&D 01 | | R&D 01 | | R&D 01 | |
| Dissolution (n=3) 900ml of water Paddles @ 50rpm | Time (min) | %LC | individuals | %LC | individuals | %LC | individuals | %LC | individuals |
| | 10 | 50 | 45, 53, 51 | 67 | 67, 68, 67 | 70 | 78, 51, 81 | 60 | 65, 47, 70 |
| | 15 | 52 | 47, 56, 54 | 71 | 69, 74, 70 | 73 | 80, 53, 85 | 83 | 84, 81, 85 |
| | 30 | 55 | 50, 57, 57 | 72 | 70, 76, 71 | 73 | 81, 54, 85 | 88 | 87, 86, 88 |
| | 45 | 56 | 60, 56, 58 | 73 | 71, 76, 72 | 73 | 80, 54, 85 | 87 | 88, 86, 86 |
| | 60 (ramp) | 58 | 54, 60, 60 [a] | 75 | 73, 76, 75 [a] | 76 | 80, 64, 84 [a] | 87 | 87, 86, 86 [a] |
| | Method revision | R&D 3 | | R&D 3 | | R&D 3 | | R&D 3 | |
| | Observations | Coning observed after 5 minutes; all tablets were completely disintegrated before 10 min. | | Coning observed after 5 minutes; all tablets were completely disintegrated before 10 min. | | Coning observed after 5 minutes; all tablets were completely disintegrated before 10 min. | | Coning observed after 5 minutes; all tablets were completely disintegrated before 10 min. | |
| Dissolution (n=3) 900ml of 0.1N HCl Paddles @ 50rpm | Time (min) | %LC | individuals | %LC | individuals | %LC | individuals | %LC | individuals |
| | 10 | 88 | 85, 88, 90 | 88 | 88, 78, 92 | 75 | 88, 49, 87 | 34 | 20, 29, 51 |
| | 15 | 94 | 92, 94, 95 | 95 | 94, 95, 95 | 84 | 86, 82, 93 | 67 | 54, 63, 85 |
| | 30 | 96 | 95, 97, 96 | 94 | 94, 91, 96 | 90 | 99, 76, 96 | 93 | 95, 88, 95 |
| | 45 | 97 | 97, 98, 96 | 96 | 95, 96, 97 | 93 | 99, 83, 97 | 97 | 102, 92, 98 |
| | 60 (ramp) | 98 | 98, 98, 97 | 96 | 95, 96, 97 | 101 | 103, 100, 101 | 99 | 103, 93, 99 |
| | Method revision | R&D 01 | | R&D 01 | | R&D 01 | | R&D 01 | |
| | Observations | Coning observed after 5 minutes; all tablets were completely disintegrated before 10 min. | | Coning observed after 5 minutes; all tablets were completely disintegrated before 10 min. | | Coning observed after 5 minutes; all tablets were completely disintegrated before 10 min. | | Coning observed after 5 minutes; all tablets were completely disintegrated before 10 min. | |

Figure 15: Dissolution profile of 12.5 mg, 25 mg, and 100 mg tablet prototypes in 0.1 HCl
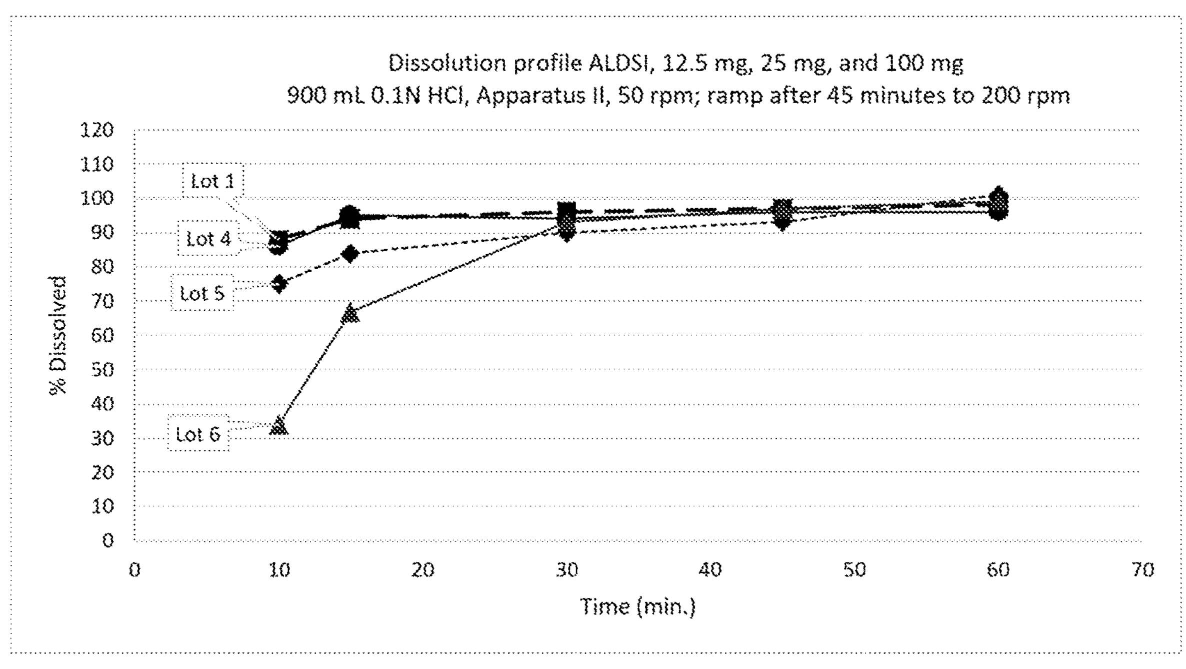

Figure 16: Summary of Analytical data for prototype formulations

| **Lot** | | **11** | | **13** | | **15** | |
|---|---|---|---|---|---|---|---|
| **Dose strength** *(mg/tablet)* | | 12.5 | | 12.5 | | 12.5 | |
| **Description** *(Visual)* | | White round biconvex film coated tablets | | White round biconvex film coated tablets | | White round biconvex film coated tablets | |
| **Assay** [A] | %LC | 98.8 (97.2, 100.4) | | 98.7 (98.7,98.6) | | **88.5** (88.5, 88.5) | |
| | Method revision | R&D03 | | R&D03 | | R&D03 | |
| **Related Substances** *% LC* | **Total Impurities:** | No impurity ≥0.05% | | No impurity ≥0.05% | | No impurity ≥0.05% | |
| | Method revision | R&D03 | | R&D03 | | R&D03 | |
| **Dissolution** *(n=3)* *900 ml of water Paddles @ 50 rpm* | Time (min) | %LC | *individuals* | %LC | *individuals* | %LC | *individuals* |
| | 10 | 84 | 92, 83, 78 | 96 | 96, 95, 96 | 90 | 91, 93, 86 |
| | 15 | 87 | 93, 87, 81 | 98 | 99, 96, 97 | 92 | 92, 96, 87 |
| | 30 | 89 | 94, 88, 84 | 99 | 100, 99, 97 | 92 | 92, 96, 88 |
| | 45 | 90 | 95, 90, 86 | 99 | 100, 99, 98 | 92 | 92, 96, 88 |
| | 60 (ramp) | 93 | 97, 92, 90 | 99 | 100, 99, 97 | 92 | 92, 95, 88 |
| | Method revision | R&D 01 | | R&D 01 | | R&D 01 | |
| | Observations | Coning observed; all tablets were completely disintegrated at 10 min; back pressure was observed during filtration. | | Coning observed; all tablets were completely disintegrated at 10 min; back pressure was observed during filtration. | | All tablets were completely disintegrated at 10 min, back pressure was observed during filtration. | |
| **Dissolution** *(n=3)* *900 ml of 0.1N HCl Paddles @ 50 rpm* | Time (min) | %LC | *individuals* | %LC | *individuals* | %LC | *individuals* |
| | 10 | 84 | 80, 81, 91 | 86 | 84, 85, 90 | 85 | 81, 85, 87 |
| | 15 | 87 | 84, 85, 93 | 96 | 99, 93, 97 | 89 | 87, 91, 88 |
| | 30 | 90 | 88, 89, 94 | 98 | 101, 94, 98 | 89 | 87, 93, 88 |
| | 45 | 92 | 90, 91, 95 | 98 | 101, 94, 98 | 89 | 87, 92, 89 |
| | 60 (ramp) | 98 | 97, 98, 99 | 97 | 101, 94, 98 | **89** | 87, 92, 88 |
| | Method revision | R&D 01 | | R&D 01 | | R&D 01 | |
| | Observations | Coning observed; all tablets were completely disintegrated at 10 min. | | All tablets were completely disintegrated at 10 min. | | Tablets not completely disintegrated at 10 min. | |

| **Lot #** | | *12.5 mg tablets* | | |
|---|---|---|---|---|
| | | **11** | **13** | **15** |
| **Content Uniformity** *USP <905>* | Tablet # | %LC | %LC | %LC |
| | 1 | 95.3 | 95.9 | 93.9 |
| | 2 | 98.1 | 95.6 | 90.9 |
| | 3 | 98.5 | 89.9 | 91.0 |
| | 4 | 100.3 | 97.9 | 88.9 |
| | 5 | 99.3 | 91.7 | 88.8 |
| | 6 | 97.2 | 99.3 | 87.1 |
| | 7 | 100.5 | 99.4 | 93.7 |
| | 8 | 99.0 | 97.4 | 87.6 |
| | 9 | 97.4 | 96.8 | 87.1 |
| | 10 | 95.1 | 97.9 | 87.2 |
| | **Average** | **98.1** | **96.2** | **89.6** |
| | %RSD | 1.9 | 3.3 | 3.0 |
| | Min | 95.1 | 89.9 | 87.1 |
| | Max | 100.5 | 99.4 | 93.9 |
| | **AV** | **4.9** | **9.8** | **15.3** |
| | Method revision | R&D 0 | R&D 0 | R&D 0 |

Figure 17: Dissolution profile of 12.5 mg tablet prototypes in water
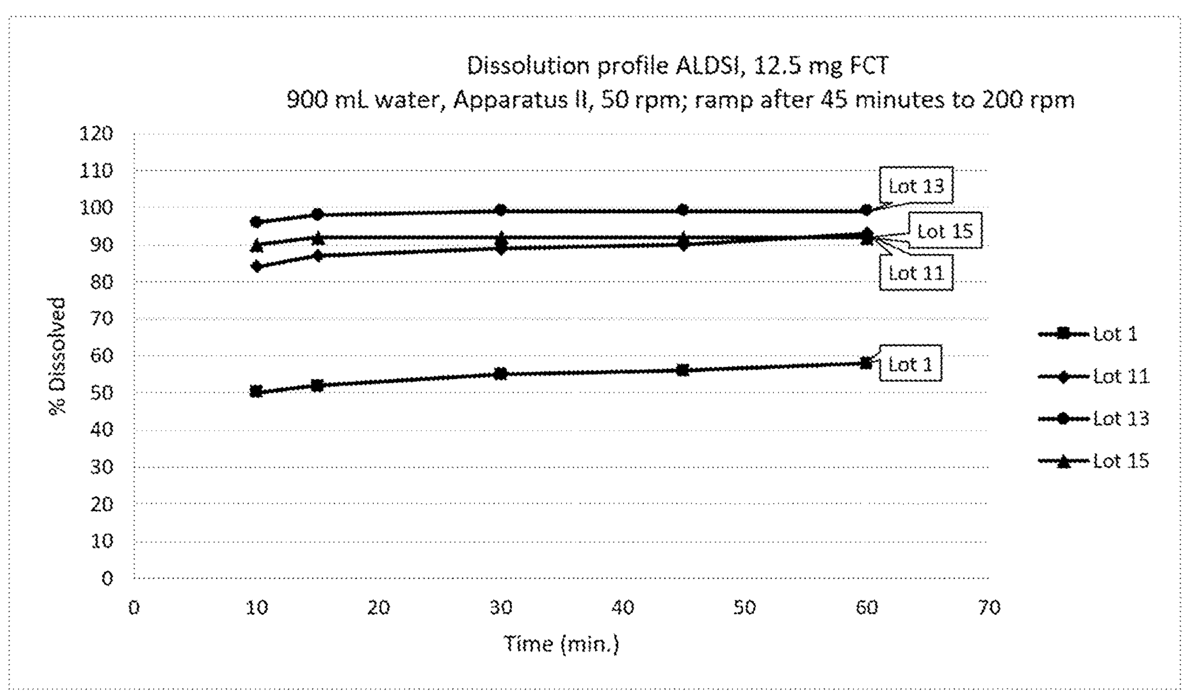
Figure 18: Dissolution profile of 12.5 mg tablet prototypes in 0.1N HCl
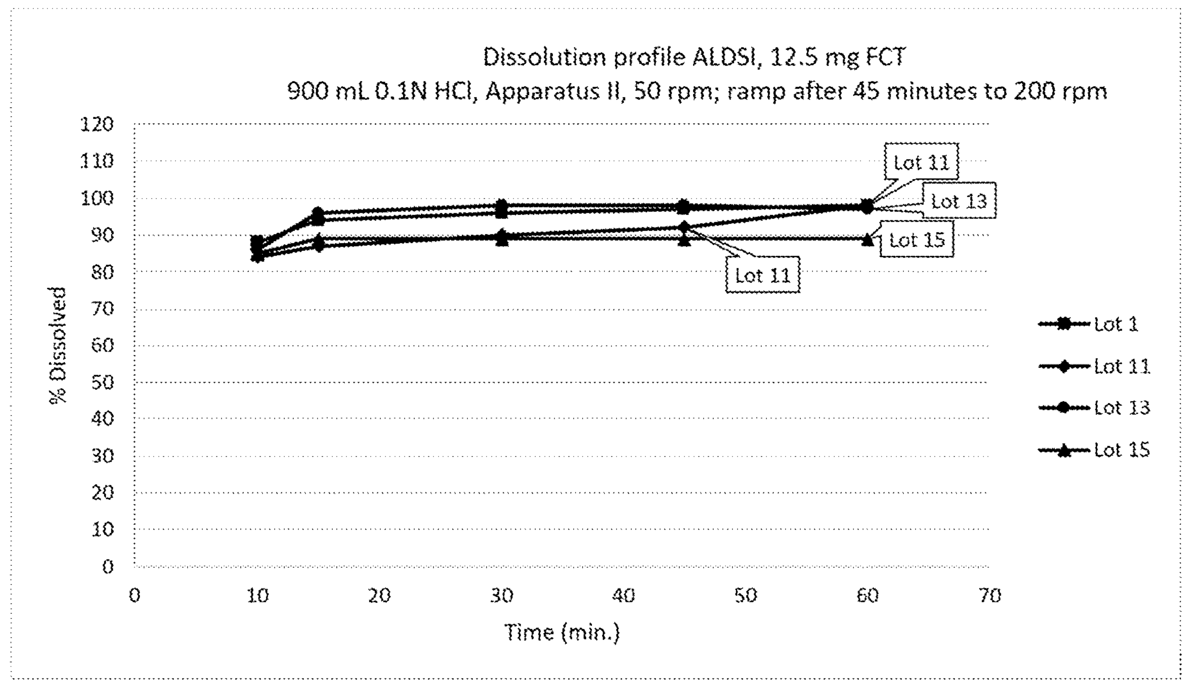

SOLUBLE PHARMACEUTICAL COMPOSITIONS COMPRISING SALTS OF DISUBSTITUTED 1, 2, 4-TRIAZINE COMPOUND

CROSS-REFERENCE TO RELATED APPLICATIONS

This application is a § 371 national stage of PCT International Application No. PCT/IB2022/056709, filed Jul. 20, 2022, claiming the benefit of U.S. Provisional Patent Application No. 63/223,711, filed Jul. 20, 2021, the entire contents of each of which are hereby incorporated herein by reference into the subject application.

Throughout this application, various publications are referenced, including referenced in parenthesis. The disclosures of all publications mentioned in this application in their entireties are hereby incorporated by reference into this application in order to provide additional description of the art to which this invention pertains and of the features in the art which can be employed with this invention.

FIELD OF THE INVENTION

The present invention is directed to, inter alia, pharmaceutical compositions and processes for producing such pharmaceutical compositions.

BACKGROUND OF THE INVENTION

U.S. Pat. Nos. 10,029,993 and 10,329,263, the disclosures of which are incorporated by reference herein in their entirety, describe CYP11β2 beta hydroxylase inhibitors. To facilitate administration of such inhibitors to human subjects, formulations with good oral absorption characteristics are needed.

SUMMARY OF THE INVENTION

Provided herein are pharmaceutical compositions comprising a salt of a compound having the formula:

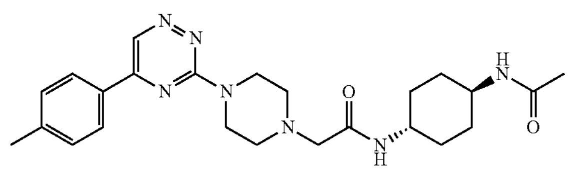

3-[4-[[trans-4-(acetoamino)cyclohexyl]carbamoylmethyl]piperazin-1-yl]-5-(p-tolyl)-1,2,4-triazine and one or more excipients, wherein the pharmaceutical composition avoids inducing disproportionation of the salt of the compound.

Provided herein are pharmaceutical compositions comprising a salt of a compound having the formula:

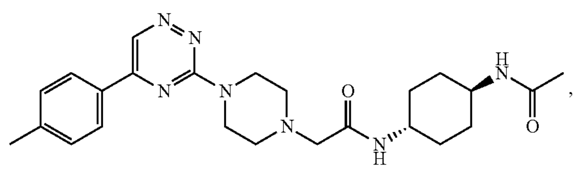

3-[4-[[trans-4-(acetoamino)cyclohexyl]carbamoylmethyl]piperazin-1-yl]-5-(p-tolyl)-1,2,4-triazine and one or more excipients, wherein the pharmaceutical composition has a dissolution profile such that more than 70% of the compound is dissolved in 15 minutes in an in vitro dissolution test of the pharmaceutical composition using USP Apparatus 2 Paddle Method at 50 rpm in a dissolution medium of water at 37° C.

These and other embodiments and aspects of the disclosure are provided in detail herein.

BRIEF DESCRIPTION OF THE DRAWINGS

FIG. 5: XRPD diffractograms of final blend and uncoated tablet for DC lot 1.

FIG. 6: XRPD diffractograms of final blend and uncoated tablet for DC lot 4.

FIG. 7: XRPD diffractograms of final blend and uncoated tablet for DC lot 5.

FIG. 8: XRPD diffractograms of at various steps of HSWG manufacturing process for lot 6.

FIG. 9: XRPD diffractograms of lot 11 final blend, uncoated tablet, and film coated tablet.

FIG. 10: XRPD diffractograms of lot 13 final blend, uncoated tablet, and film coated tablet.

FIG. 11: XRPD diffractograms of lot 15 final blend, uncoated tablet, and film coated tablet.

FIG. 12: XRPD diffractograms of lot 17 final blend, uncoated tablet (Trials #1 & #2), and film coated tablet (Trials #2).

FIG. 13: XRPD diffractograms of lot 18 final blend, uncoated tablet (Trials #1/#2 & #3), and film coated tablet (Trials #2).

FIG. 14: Summary of analytical data for prototype formulations.

FIG. 15: Dissolution profile of 12.5 mg, 25 mg, and 100 mg tablet prototypes in 0.1 HCl.

FIG. 16: Summary of analytical data for prototype formulations.

FIG. 17: Dissolution profile of 12.5 mg tablet prototypes in water.

FIG. 18: Dissolution profile of 12.5 mg tablet prototypes in 0.1N HCl.

DETAILED DESCRIPTION OF THE INVENTION

Pharmaceutical Compositions

Figure 1:
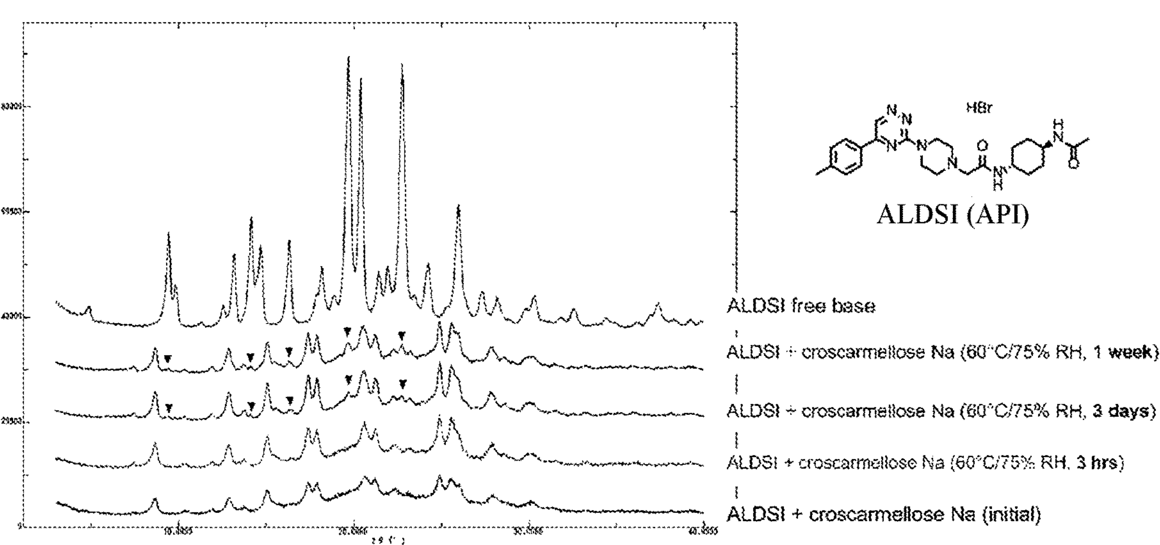
FIG. 1: Powder x-ray diffraction peaks detected from MLS-101 after 3 days of storage with a metal salt (croscarmellose Na) (storage conditions: 60° C./75% RH).

Provided herein are pharmaceutical compositions comprising a salt of a compound having the formula:

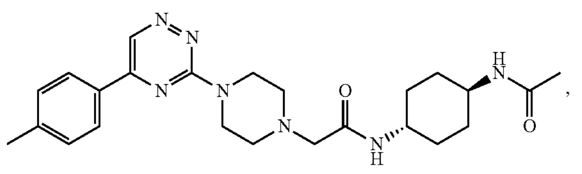

3-[4-[[trans-4-(acetoamino)cyclohexyl]carbamoylmethyl]piperazin-1-yl]-5-(p-tolyl)-1,2,4-triazine and one or more excipients, wherein the pharmaceutical composition avoids inducing disproportionation of the salt of the compound.

Also provided herein are pharmaceutical compositions comprising a salt of a compound having the formula:

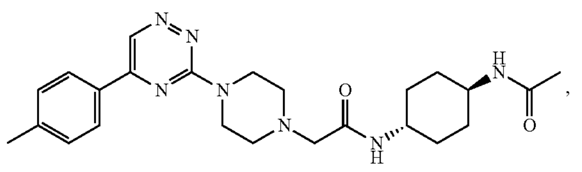

3-[4-[[trans-4-(acetoamino)cyclohexyl]carbamoylmethyl]piperazin-1-yl]-5-(p-tolyl)-1,2,4-triazine and one or more excipients, wherein the pharmaceutical composition has a dissolution profile such that more than 70%, more than 75%, more than 80%, or more than 85% of the compound is dissolved in 15 minutes in an in vitro dissolution test of the pharmaceutical composition using USP Apparatus 2 Paddle Method at 50 rpm in a dissolution medium of water at 37° C. In embodiment, the pharmaceutical composition has a dissolution profile such that more than 70% more than 75%, more than 80%, more than 85%, more than 90%, or more than 95% of the compound is dissolved in 30 minutes in an in vitro dissolution test of the pharmaceutical composition using USP Apparatus 2 Paddle Method at 50 rpm in a dissolution medium of water at 37° C.

In embodiments, the salt is an anion salt. In embodiments, the salt is a halogen anion salt. In embodiments, the salt is an HBr salt. In embodiments, the salt is a salt other than an HBr salt. In embodiments, the salt is a halogen anion salt other than an HBr salt.

In embodiments, the pharmaceutical composition does not comprise any of croscarmellose sodium, and magnesium stearate. In embodiments, the pharmaceutical composition does not comprise any of dicalcium phosphate, croscarmellose sodium, and magnesium stearate. In embodiments, the pharmaceutical composition does not comprise any of dicalcium phosphate, croscarmellose sodium, magnesium stearate, carmellose calcium, sodium stearyl fumarate, calcium stearate, and anhydrous dibasic calcium phosphate. In embodiments, the pharmaceutical composition does not comprise a magnesium salt or a sodium salt. In embodiments, the pharmaceutical composition does not comprise a calcium salt, a magnesium or a sodium salt. In embodiments, the pharmaceutical composition does not comprise magnesium or sodium. In embodiments, the pharmaceutical composition does not comprise calcium, magnesium or sodium. In embodiments, the pharmaceutical composition does not comprise a metal salt.

In embodiments where the salt is an HBr salt, the pharmaceutical composition does not comprise any of croscarmellose sodium, and magnesium stearate. In embodiments where the salt is an HBr salt, the pharmaceutical composition does not comprise any of dicalcium phosphate, croscarmellose sodium, and magnesium stearate. In embodiments where the salt is an HBr salt, the pharmaceutical composition does not comprise any of dicalcium phosphate, croscarmellose sodium, magnesium stearate, carmellose calcium, sodium stearyl fumarate, calcium stearate, and anhydrous dibasic calcium phosphate. In embodiments where the salt is an HBr salt, the pharmaceutical composition does not comprise a magnesium salt or a sodium salt. In embodiments where the salt is an HBr salt, the pharmaceutical composition does not comprise a calcium salt, a magnesium or a sodium salt. In embodiments where the salt is an HBr salt, the pharmaceutical composition does not comprise magnesium or sodium. In embodiments where the salt is an HBr salt, the pharmaceutical composition does not comprise calcium, magnesium or sodium. In embodiments where the salt is an HBr salt, the pharmaceutical composition does not comprise a metal salt.

In an embodiment where the salt is a salt other than an HBr salt, the pharmaceutical composition may comprise a metal salt, may comprise calcium, magnesium or sodium, may comprise a calcium salt, a magnesium salt or a sodium salt, and may comprise dicalcium phosphate, croscarmellose sodium, and magnesium stearate, carmellose calcium, sodium stearyl fumarate, calcium stearate, and anhydrous dibasic calcium phosphate. In an alternative embodiment where the salt is other than an HBr salt, the pharmaceutical composition does not comprise any of dicalcium phosphate, croscarmellose sodium, and magnesium stearate, carmellose calcium, sodium stearyl fumarate, calcium stearate, and anhydrous dibasic calcium phosphate, does not comprise a calcium salt, a magnesium salt or a sodium salt, does not comprise calcium, magnesium or sodium, or does not comprise a metal salt.

In embodiments, the salt of the compound is in solid form. In embodiments, the salt of the compound is in crystalline form. In embodiments the salt of the compound is in amorphous form. In embodiments the pharmaceutical composition comprises a mixture of the salt of the compound in crystalline and amorphous forms.

In embodiments, the pharmaceutical composition comprises one or more pharmaceutically acceptable excipients selected from the group consisting of microcrystalline cellulose, lactose, mannitol, polyvinylpyrrolidone, colloidal silicone dioxide, pregelatinized starch, low-substituted hydroxypropyl cellulose, talc, glyceryl dibehenate, and stearic acid.

In embodiments, the pharmaceutical composition comprises microcrystalline cellulose 102, mannitol 400DC, pregelatinized starch, and glyceryl dibehenate In embodiments the composition comprises from about 0.5 milligrams to about 500 milligrams of the compound. In embodiments, the pharmaceutical composition comprises from about 5 milligrams to about 150 milligrams of the compound. In embodiments to composition comprises about 12.5 milligrams to about 100 milligrams of the compound. In embodiments the pharmaceutical composition comprises 12.5 milligrams, about 25 milligrams, about 50 milligrams, or about 100 milligrams of the compound.

In embodiments, the pharmaceutical composition comprises:

a) about 30 wt % to about 60 wt % of lactose, mannitol, or a combination thereof;

b) about 25 wt % to about 50 wt % of microcrystalline cellulose;

c) about 1 wt % to about 10 wt % of polyvinylpyrrolidone, pregelatinized starch, or a combination thereof; and
d) about 1 wt % to about 10 wt % of talc, glyceryl dibehenate, colloidal silicone dioxide, or a combination of two or more thereof.

In embodiments of the pharmaceutical composition, the compound is more soluble in water than the same compound in an equivalent pharmaceutical composition comprising a calcium salt, a sodium salt or magnesium salt. In embodiments of the pharmaceutical composition, the compound is more soluble in water than the same compound in an equivalent pharmaceutical composition comprising a sodium salt or magnesium salt.

In embodiments of the pharmaceutical composition, the pharmaceutical composition has a dissolution profile such that more than 70%, more than 75%, more than 80%, or more than 70% of the compound is dissolved in 15 minutes in an in vitro dissolution test of the pharmaceutical composition using USP Apparatus 2 Paddle Method at 50 rpm in a dissolution medium of water at 37° C. In embodiment, the pharmaceutical composition has a dissolution profile such that more than 70% more than 75%, more than 80%, more than 85%, more than 90%, or more than 95% of the compound is dissolved in 30 minutes in an in vitro dissolution test of the pharmaceutical composition using USP Apparatus 2 Paddle Method at 50 rpm in a dissolution medium of water at 37° C.

In embodiments, the pharmaceutical composition avoids disproportionation in excess of 1% of the salt:

a) when stored at 25° C.+/−2° C. and 60% relative humidity (RH)+/−5% RH for 6 or 12 months;
b) when stored at 30° C.+/−2° C. and 65% RH+/−5% RH for 6 or 12 months;
c) when stored at 30° C.+/−2° C. and 75% RH+/−5% RH for 6 or 12 months; and/or
d) when stored at 40° C.+/−2° C. and 75% RH+/−5% RH for 6 months.

In embodiments, the pharmaceutical composition avoids disproportionation in excess of 5% of the salt:

a) when stored at 25° C.+/−2° C. and 60% relative humidity (RH)+/−5% RH for 6 or 12 months;
b) when stored at 30° C.+/−2° C. and 65% RH+/−5% RH for 6 or 12 months;
c) when stored at 30° C.+/−2° C. and 75% RH+/−5% RH for 6 or 12 months; and/or
d) when stored at 40° C.+/−2° C. and 75% RH+/−5% RH for 6 months.

In embodiments, the pharmaceutical composition avoids disproportionation in excess of 10% of the salt:

a) when stored at 25° C.+/−2° C. and 60% relative humidity (RH)+/−5% RH for 6 or 12 months;
b) when stored at 30° C.+/−2° C. and 65% RH+/−5% RH for 6 or 12 months;
c) when stored at 30° C.+/−2° C. and 75% RH+/−5% RH for 6 or 12 months; and/or
d) when stored at 40° C.+/−2° C. and 75% RH+/−5% RH for 6 months.

In embodiments, the aforementioned storage conditions are in a closed container. In embodiments, the aforementioned storage conditions are in an open container.

In embodiments, after storage under any of the aforementioned conditions, the pharmaceutical composition has a dissolution profile such that more than 70%, more than 75%, more than 80%, or more than 85% of the compound is dissolved in 15 minutes in an in vitro dissolution test of the pharmaceutical composition using USP Apparatus 2 Paddle Method at 50 rpm in a dissolution medium of water at 37° C. In embodiment, after storage under any of the aforementioned conditions, the pharmaceutical composition has a dissolution profile such that more than 70% more than 75%, more than 80%, more than 85%, more than 90%, or more than 95% of the compound is dissolved in 30 minutes in an in vitro dissolution test of the pharmaceutical composition using USP Apparatus 2 Paddle Method at 50 rpm in a dissolution medium of water at 37° C.

In embodiments, the pharmaceutical composition comprises from about 5 milligrams to about 20 milligrams of the compound, preferably from about 10 milligrams to about 15 milligrams of the compound, or more preferably about 12.5 milligrams of the compound. In embodiments, the pharmaceutical composition comprises:

a) about 1 wt % to about 8 wt % of the compound;
b) about 50 wt % to about 60 wt % of lactose, mannitol, or a combination thereof;
c) about 25 wt % to about 40 wt % of microcrystalline cellulose;
d) about 1 wt % to about 10 wt % of polyvinylpyrrolidone, pregelatinized starch, or a combination thereof; and
e) about 1 wt % to about 10 wt % of talc, glyceryl dibehenate, colloidal silicone dioxide, or a combination of two or more thereof.

In embodiments, the pharmaceutical composition comprises from about 15 milligrams to about 35 milligrams of the compound, preferably from about 20 milligrams to about 30 milligrams of the compound, or more preferably about 25 milligrams of the compound. In embodiments, the pharmaceutical composition comprises:

a) about 5 wt % to about 15 wt % of the compound;
b) about 30 wt % to about 50 wt % of mannitol;
c) about 30 wt % to about 50 wt % of microcrystalline cellulose;
d) about 1 wt % to about 10 wt % of pregelatinized starch; and
e) about 1 wt % to about 5 wt % of glyceryl dibehenate, colloidal silicone dioxide, or a combination thereof.

In embodiments, the pharmaceutical composition comprises from about 80 milligrams to about 120 grams of the compound, preferably from about 95 milligrams to about 105 milligrams of the compound, or more preferably about 100 milligrams of the compound. In embodiments, the pharmaceutical composition comprises:

a) about 30 wt % to about 40 wt % of the compound;
b) about 20 wt % to about 30 wt % of mannitol;
c) about 20 wt % to about 40 wt % of microcrystalline cellulose;
d) about 1 wt % to about 10 wt % of pregelatinized starch;
e) about 1 wt % to about 5 wt % of glyceryl dibehenate, colloidal silicone dioxide, or a combination thereof.

In embodiments of any of the above pharmaceutical compositions, the pharmaceutical composition comprises between 3 wt % and 8 wt % of stearic acid, preferably about 5 wt % stearic acid.

Tablets

In embodiments, the pharmaceutical composition is a tablet. In embodiments, the tablet comprises a coating. In embodiments, the coating comprises hydroxypropylmethyl cellulose, polyvinyl alcohol, or a combination thereof.

Processes for Producing the Pharmaceutical Compositions

Provided herein is a process for making a pharmaceutical composition comprising a salt of a compound having the formula:

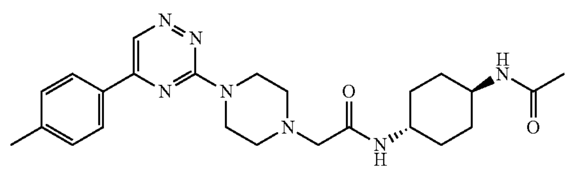

3-[4-[[trans-4-(acetoamino)cyclohexyl]carbamoylmethyl]piperazin-1-yl]-5-(p-tolyl)-1,2,4-triazine and one or more excipients, wherein the pharmaceutical composition avoids inducing disproportionation of the salt of the compound and/or the pharmaceutical composition has a dissolution profile such that more than 70%, more than 75%, more than 80%, or more than 85% of the compound is dissolved in 15 minutes in an in vitro dissolution test of the pharmaceutical composition using USP Apparatus 2 Paddle Method at 50 rpm in a dissolution medium of water at 37° C., comprising:

a) obtaining a salt of a compound having the formula:

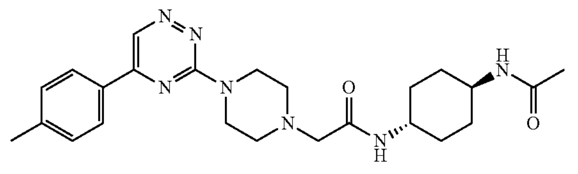

3-[4-[[trans-4-(acetoamino)cyclohexyl]carbamoylmethyl]piperazin-1-yl]-5-(p-tolyl)-1,2,4-triazine b) mixing the salt with one or more excipients to thereby produce the pharmaceutical composition.

In an embodiment, the pharmaceutical composition has a dissolution profile such that more than 70%, more than 75%, more than 80%, or more than 85% of the compound is dissolved in 30 minutes in an in vitro dissolution test of the pharmaceutical composition using USP Apparatus 2 Paddle Method at 50 rpm in a dissolution medium of water at 37° C.

In an embodiment, the salt is an anion salt. In an embodiment, the salt is a halogen anion salt. In an embodiment, the salt is an HBr salt.

In embodiments of the above process, step b) comprises:

i) blending the salt with one or more excipients; and ii) roller compaction of the product of step i); and iii) milling the product of step ii).

In embodiments, one or more excipients of step i) comprises stearic acid, more preferably about 5 wt % stearic acid. In embodiments, step b) further comprises a step of blending the product of step iii) with one or more additional excipients, preferably wherein the one or more additional excipients comprise stearic acid.

In an embodiment, the process further comprises tableting the pharmaceutical composition to produce tablet cores. In an embodiment, the process further comprises film-coating the tablet cores.

In an embodiment of the process, the one or more excipients do not comprise any of croscarmellose sodium, and magnesium stearate. In an embodiment of the process, the one or more excipients do not comprise any of dicalcium phosphate, croscarmellose sodium, and magnesium stearate. In an embodiment of the process, the one or more excipients do not comprise any of dicalcium phosphate, croscarmellose sodium, magnesium stearate, carmellose calcium, sodium stearyl fumarate, calcium stearate, and anhydrous dibasic calcium phosphate. In an embodiment of the process, the one or more excipients do not comprise a magnesium salt or a sodium salt. In an embodiment of the process, the one or more excipients do not comprise a calcium salt, a magnesium salt or a sodium salt. In an embodiment of the process, the one or more excipients do not comprise magnesium or sodium. In an embodiment of the process, the one or more excipients do not comprise calcium, magnesium or sodium. In an embodiment of the process, the one or more excipients do not comprise a metal salt.

In an embodiment of the process, the salt of the compound is in solid form. In embodiments, the salt of the compound is in crystalline form. In embodiments, the salt of the compound is in amorphous form. In embodiments of the process, the pharmaceutical composition comprises a mixture of the salt of the compound in crystalline and amorphous forms.

In an embodiment of the process, the one or more excipients are selected from the group consisting of microcrystalline cellulose, lactose, mannitol, polyvinylpyrrolidone, colloidal silicone dioxide, pregelatinized starch, low-substituted hydroxypropyl cellulose, talc, glyceryl dibehenate, and stearic acid.

In an embodiment of the process, the one or more excipients comprise microcrystalline cellulose 102, mannitol 400DC, pregelatinized starch, and glyceryl dibehenate.

In an embodiment of the process, the pharmaceutical composition comprises:

a) about 30 wt % to about 60 wt % of lactose, mannitol, or a combination thereof;

b) about 25 wt % to about 50 wt % of microcrystalline cellulose;

c) about 1 wt % to about 10 wt % of polyvinylpyrrolidone, pregelatinized starch, or a combination thereof;

d) about 1 wt % to about 10 wt % of talc, glyceryl dibehenate, colloidal silicone dioxide, or a combination of two or more thereof.

In embodiments of the process, the pharmaceutical composition comprises one or more or all of the following features:

a) between 20 wt % and 30 wt % of microcrystalline cellulose;

b) between 20 wt % and 30 wt % of D-Mannitol; and c) between 3 wt % and 8 wt % of stearic acid.

Methods and Compositions for Use

Also provided herein is a method of treating hypertension and/or reducing blood pressure in a hypertensive subject, the method comprising administering to the hypertensive subject any of the compositions described herein.

Also provided herein is a method of inhibiting CYP11β2 beta hydroxylase in a subject, the method comprising administering to the subject the composition of any of the compositions described herein.

Also provided herein are any of the compositions described herein for use in treating hypertension and/or reducing blood pressure in a hypertensive subject.

Also provided herein are any of the compositions described herein for use in inhibiting CYP11β2 beta hydroxylase in a subject.

Definitions

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

In the discussion unless otherwise stated, adjectives such as "substantially" and "about" modifying a condition or relationship characteristic of a feature or features of an embodiment of the invention, are understood to mean that the condition or characteristic is defined to within tolerances that are acceptable for operation of the embodiment for an application for which it is intended. Unless otherwise indicated, the word "or" in the specification and claims is considered to be the inclusive "or" rather than the exclusive or, and indicates at least one of and any combination of items it conjoins.

It should be understood that the terms "a" and "an" as used above and elsewhere herein refer to "one or more" of the enumerated components. It will be clear to one of ordinary skill in the art that the use of the singular includes the plural unless specifically stated otherwise. Therefore, the terms "a," "an" and "at least one" are used interchangeably in this application.

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

In the description and claims of the present application, each of the verbs, "comprise," "include" and "have" and conjugates thereof, are used to indicate that the object or objects of the verb are not necessarily a complete listing of components, elements or parts of the subject or subjects of the verb. Other terms as used herein are meant to be defined by their well-known meanings in the art.

As used herein "ALDSI" and "MLS-101" refers to the hydrobromide (HBr) salt of the disubstituted 1,2,4-Triazine compound which is represented by Formula (A):

(A)

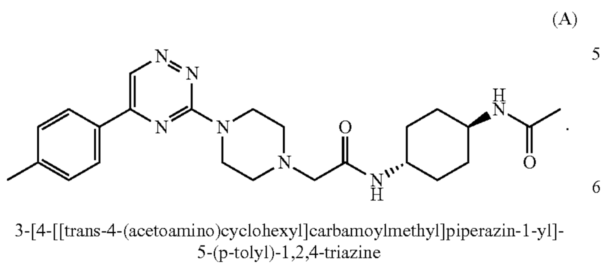

3-[4-[[trans-4-(acetoamino)cyclohexyl]carbamoylmethyl]piperazin-1-yl]-5-(p-tolyl)-1,2,4-triazine Weights and/or strengths of "ALDSI", "MLS-101," and "the compound" of the invention refer to the weight of the free base in the HBr salt and not the weight of the HBr salt.

The compound of Formula (A) and pharmaceutically acceptable salts thereof can be made by processes described, for example, in U.S. Pat. No. 10,029,993 and European Publication No. 3549935, the disclosures of which are incorporated by reference herein in their entirety.

This invention relates to the surprising discovery that MLS-101 undergoes disproportionation when combined with pharmaceutical excipients containing metal salts, in particular calcium salts, magnesium salts and sodium salts. Accordingly, each pharmaceutical composition of the invention "does not comprise" excipients containing metal salts (and in particular "does not comprise" calcium salts, magnesium salts or sodium salts) in order to avoid disproportionation of MLS-101 and preserve its aqueous solubility. A person skilled in the art will appreciate that a pharmaceutical composition would be within the scope of the invention when it contains trace amounts of such metal salts if such trace amounts do not cause disproportionation above an acceptable threshold limit. Accordingly, the use of the term "does not comprise" encompasses amounts of metal salts that are low enough so as to not cause disproportionation above an acceptable threshold limit. As used herein, 10% disproportionation is the acceptable threshold limit for disproportionation. In some embodiments a lower threshold limit of disproportionation may be preferred. For example, in embodiments of the invention, the composition avoids disproportionation in excess of 9%, 8%, 7%, 6%, 5%, 4%, 3%, 2%, or 1%.

The pharmaceutical compositions of the invention may include a "therapeutically effective amount" or a "prophylactically effective amount" of a compound of the invention. A "therapeutically effective amount" refers to an amount effective, at dosages and for periods of time necessary, to achieve the desired therapeutic result. A therapeutically effective amount of the compound may vary according to factors such as the disease state, age, sex, and weight of the individual. A therapeutically effective amount is also one in which any toxic or detrimental effects of the compound are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

General

For the foregoing embodiments, each embodiment disclosed herein is contemplated as being applicable to each of the other disclosed embodiment.

As used herein, all headings are simply for organization and are not intended to limit the disclosure in any manner. The content of any individual section may be equally applicable to all sections. All combinations of the various elements disclosed herein are within the scope of the invention.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

Examples are provided below to facilitate a more complete understanding of the invention. The following examples illustrate the exemplary modes of making and practicing the invention. However, the scope of the invention is not limited to specific embodiments disclosed in these Examples, which are for purposes of illustration only.

EXAMPLES

Example 1

Risk Assessment of Salt Disproportionation

ALDSI-derived peaks were detected after 3 days of storage of ALDSI with a metal salt (croscarmellose Na). (storage conditions: 60° C./75% RH)

As shown in FIG. 1, ALDSI has a high propensity toward disproportionation in the presence of a metal salt.

Study of Salt Disproportionation and Strategy to Reduce the Disproportionation Risk After the discovery of the salt disproportionation of ALDSI in the presence of a metal salt, a strategy to reduce the disproportionation risk was sought.

Summary of Results:

The risk of salt disproportionation may be reduced by the appropriate selection of excipients.

Testing the Effects of Possible Factors on Salt Disproportionation

Temperature and Humidity

Sample: API (ALDSI)

Storage conditions: 25° C./60% RH, 40° C./75% RH, and 60° C./75% RH (relative humidity) in an open container Sampling time points: 3 days and 1 week Dissolution Test of ALDSI Test method: JP Apparatus for Paddle Method (Apparatus 2)

Revolutions: 50 rpm for 0-30 min, and 250 rpm for 30 min.

Dissolution medium: JP Second Fluid for dissolution test (A mixture of phosphate buffer solution (pH 6.8) and water (1:1), as described in the Japanese Pharmacopoeia.)

Results

Figure 2:
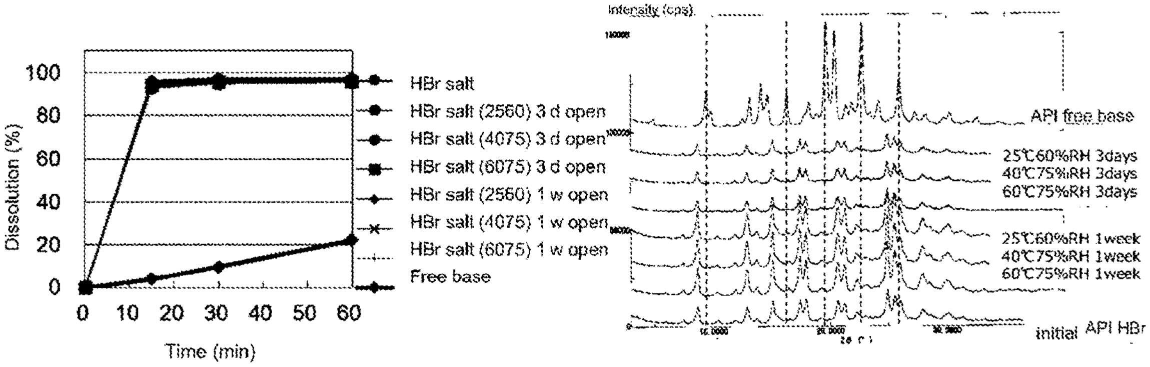
FIG. 2: Dissolution Test of API (left) and X-Ray Diffraction of API (right).

ALDSI showed no delay of dissolution or appearance of new peaks on XRPD (see FIG. 2).

Conclusion

There is a minimal risk of salt disproportionation due to temperature and humidity in the absence of excipients.

Pharmaceutical Process

Effect of Compression

API alone was compressed at 300, 600, and 900 kilograms of force (i.e. about 2942, 5884, and 8826 Newtons, respectively) to evaluate dissolution.

a) There were no differences in dissolution among samples.

b) There were no changes in dissolution over time when samples were stored at 60° C./75% RH (for 3 days or 1 week).

Conclusion: Compression has minimal effect on the risk of salt disproportionation.

Effect of Wet Gramilation

API alone was kneaded with large, middle, and small amounts of water to evaluate dissolution.

a) There were no differences in dissolution among samples.

Conclusion: Wet granulation conditions have minimal effect on the risk of salt disproportionation.

Effect of Grinding Conditions

API alone was ground for 1, 3, 20, and 30 min to evaluate dissolution.

a) There were no differences in dissolution among samples.

b) There were no changes in dissolution over time when samples were stored at 60° C./75% RH (for 3 days or 1 week).

Conclusion: Grinding may have minimal effect on the risk of salt disproportionation.

Disproportionation Due to Commonly Used Excipients

Formulation Conditions

API and excipient at a ratio of 1:1 (w/w)

Mixed in a mortar (for about 10 min without applying force)

Storage Conditions

60° C./75% RH in open container for 1 week

Tests

X-ray diffraction (XRD)

Residues after dissolution test:

a) Samples without residues were considered not to undergo disproportionation as the water solubility markedly decreases after salt disproportionation. Yellow residues were considered to represent salt disproportionation as ALDSI free base is yellow in color. White residues were considered an insoluble excipients and no salt disproportionation as ALDSI free base.

Results

Potential risk of salt disproportionation due to interaction with metal salts was shown.

TABLE 1

Excipients and their effect on salt disproportionation

| | Excipients | | XRD | Residues after dissolution |
|---|---|---|---|---|
| Disintegrants | Croscarmellose Na (Ac-Di-Sol) | Metal salt | Salt disproportionation | Yellow residue |
| | Carmellose Ca (ECG505) | Metal salt | No changes | Yellow residue |
| | Carmellose (NS-300) | — | No changes | White residue |
| | L-HPC | — | No changes | No residues |

TABLE 1-continued

| Excipients and their effect on salt disproportionation | | | | |
|---|---|---|---|---|
| Excipients | | | XRD | Residues after dissolution |
| Lubricants | Mg Stearate | Metal salt | Salt disproportionation | Yellow residue |
| | Sodium stearyl fumarate | Metal salt | Salt disproportionation | Yellow residue |
| | Talc | — | No changes | White residue |
| | Ca stearate | Metal salt | No changes | Yellow residue |
| | Stearic acid | — | No changes | No residues |
| | Hydrogenated oil | — | No changes | No residues |
| | Sucrose stearate | — | No changes | No residues |
| Diluent | Microcrystalline cellulose | — | No changes | White residue |
| | Anhydrous Dibasic Calcium Phosphate | Metal salt | No changes | Yellow residue |

Stability Test I of 10% API Capsules

Formulation of 10% API Capsules

Metal salt-free excipients were selected.

Formulation Method

D-Mannitol and talc were mixed and sieved. The API was added to the sieved mixture, blended, sieved, and filled in HPMC capsules.

TABLE 2

| Ingredients in 10% API capsule | |
|---|---|
| Ingredients | Content (mg) |
| ALDSI | 11.8 (salt) |
| D-Mannitol (Pearitol 100SD) | 85.2 |
| Talc | 3 |
| Subtotal | 100 |

Stability Test II of 10% API Capsules

Figure 3:
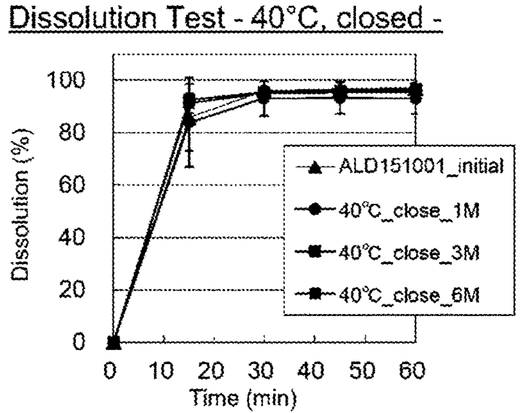
FIG. 3: Results of a dissolution test of the 10% API capsules under various conditions.
Figure 3:
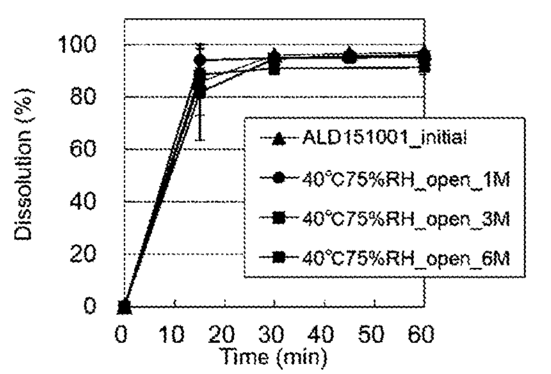
Figure 3:
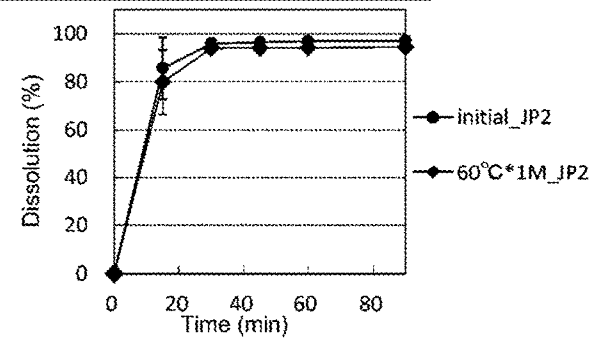

FIG. 3 shows the results of a dissolution test of the 10% API capsules under various conditions.

Conclusions

There was no risk of delayed dissolution or increased related substances in three formulations tested. 10% API capsules formulated with excipients considered not to cause disproportionation may be a pharmaceutical formulation with a low risk of salt disproportionation.

Study I of Tablets (Formulations)

Formulations

To design a formulation that can avoid the risk of salt disproportionation, low-substituted hydroxypropyl cellulose (L-HPC) and 3 lubricants were selected, which were considered not to have risk of salt disproportionation based on the results of the study presented above ("Disproportionation due to commonly used excipients.")

Formulation Method

API granules, a disintegrant, and lubricants were mixed in a polyethylene bag. After confirming pressure dependency, the mixture was subjected to sequential tableting (900 kilogram of force, i.e. about 8826 Newtons).

TABLE 3

| Purity Test Results | | | | | | | | | | | | | | |
|---|---|---|---|---|---|---|---|---|---|---|---|---|---|---|
| | Storage | Storage | Storage | Individual related substances (%) RRT (%) | | | | | | | | | | Total related |
| Lot No. | conditions | container | period | 0.91 | 0.95 | 0.96 | 0.98 | 1.06 | 1.18 | 1.19 | 1.34 | 1.72 | 1.92 | substances |
| ALDSI alone | Initial | — | — | | 0.10 | 0.04 | 0.11 | | 0.47 | 0.03 | | | | 0.75 |
| ALD1001 | Initial | — | — | | 0.11 | 0.04 | 0.11 | | 0.44 | | | | | 0.70 |
| | 60° C. | Glass bottle (amber) | 1 M | | 0.09 | 0.04 | 0.11 | | 0.44 | | | | | 0.68 |
| | 40° C./ 75% RH | Glass bottle (amber) Tightly closed | 1 M | | 0.11 | 0.04 | 0.11 | | 0.44 | | | | | 0.70 |
| | | | 3 M | | 0.10 | 0.04 | 0.12 | | 0.44 | | | | | 0.70 |
| | | | 6 M | | 0.11 | 0.05 | 0.12 | 0.03 | 0.48 | 0.02 | 0.03 | 0.03 | 0.02 | 0.89 |
| | | Glass bottle (amber) Open | 1 M | | 0.11 | 0.04 | 0.12 | | 0.45 | | | | | 0.72 |
| | | | 3 M | | 0.10 | 0.04 | 0.11 | | 0.45 | | | | | 0.70 |
| | | | 6 M | 0.02 | 0.11 | 0.05 | 0.12 | 0.03 | 0.48 | 0.02 | 0.03 | 0.03 | 0.02 | 0.91 |

TABLE 4

| Formulations | | | | Lot No. | | |
|---|---|---|---|---|---|---|
| Ingredients | | Grade | Manufacturer | A7 Content (mg) | A9 Content (mg) | A10 Content (mg) |
| API | Ground API (Free base equivalent) | — | MTPC | 11.8 (10.0) | 11.8 (10.0) | 11.8 (10.0) |
| Diluent | D-Mannitol | JP | B Food Science | 80.2 | 80.2 | 80.2 |
| Binder | HPC | HPC-SL | Nippon Soda | 3.0 | 3.0 | 3.0 |
| Disintegrant | L-HPC | LH-B1 | Shin-Etsu Chemical | 5.0 | 5.0 | 5.0 |
| Lubricants | Stearic acid | — | Merck | 3.0 | — | — |
| | Sucrose stearate | S-370FU | Mitsubishi-Chemical Foods | — | 3.0 | — |
| | Hydrogenated oil | Lubriwax ® 101 | Freund Corporation | — | — | 3.0 |
| Total | | | | 103.0 | 103.0 | 103.0 |

Study II of Tablets (Stability Test Results)

Dissolution Test Results

Dissolution after storage at 25° C. in closed, 40° C./75% RH in open and closed containers for 1 month: No changes from the initial value in any formulations.

Reason for reduced dissolution after storage at 60° C.: the lubricants in the tablets were melted as tablets were stored at a temperature near the melting points of the individual lubricants.

Figure 4:
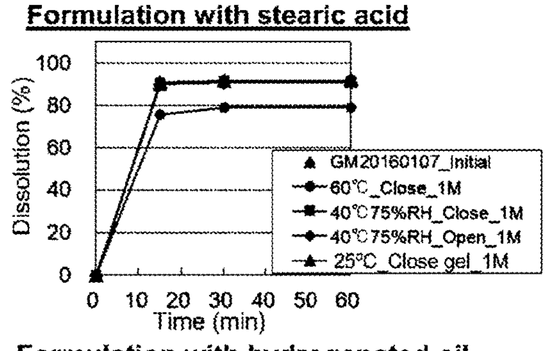
FIG. 4: Results of a dissolution test of tablet formulations after storage at 25° C. in closed, 40° C./75% RH in open and closed containers.
Figure 4:
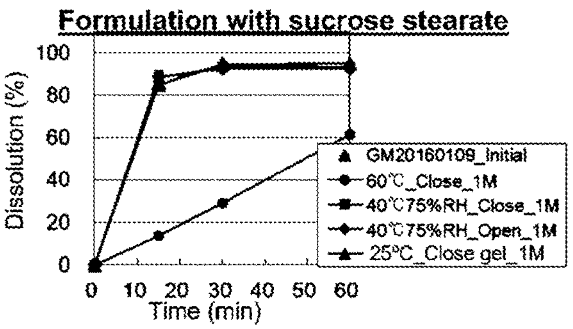
Figure 4:
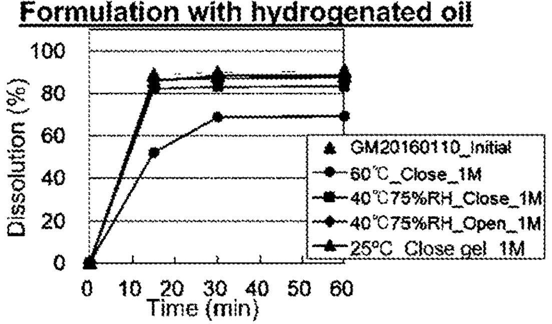

FIG. 4 shows the dissolution test results.

Purity Test Results

All formulations showed no change from initial value under all storage conditions tested.

Example 2

Introduction

This example documents the formulation development of 12.5, 25, and 100 mg MLS-101 film coated tablet dosage form with immediate release characteristics.

The physicochemical properties of MLS-101 were previously evaluated and no major issues were identified such that it was suggested that the compound could be formulated either by direct compression or granulation (dry and wet) processes.

The information provided from the formulation development activities and laboratory analyses of different formu-

TABLE 5

Purity Test Results

| Formulation | Storage conditions | Storage container | Storage period | Individual related substances (%) RRT (%) 0.79 | 0.81 | 0.85 | 0.92 | 0.94 | 0.97 | 1.09 | 1.13 | 1.35 | 1.43 | 1.69 | Total related substances |
|---|---|---|---|---|---|---|---|---|---|---|---|---|---|---|---|
| ALDSI | Initial | — | — | | 0.11 | 0.02 | | | | 0.02 | 0.02 | 0.02 | 0.02 | 0.02 | 0.23 |
| Stearic acid | Initial | — | — | 0.02 | 0.10 | 0.02 | | | | 0.02 | | 0.02 | 0.02 | 0.02 | 0.22 |
| | 60° C. | Glass bottle (amber) | 2 W | 0.02 | 0.10 | 0.04 | 0.02 | | 0.03 | 0.02 | 0.02 | 0.02 | | 0.02 | 0.29 |
| | | Tightly closed | 1 M | 0.02 | 0.10 | 0.04 | 0.02 | 0.02 | 0.02 | | | 0.02 | 0.02 | 0.02 | 0.28 |
| | 40° C./ 75% RH | Glass bottle (amber) Tightly closed | 1 M | 0.02 | 0.10 | 0.03 | 0.02 | | | 0.02 | 0.02 | 0.02 | | 0.02 | 0.25 |
| | | Glass bottle (amber) Open | 1 M | 0.02 | 0.09 | 0.03 | 0.02 | 0.02 | 0.02 | | | 0.02 | | 0.02 | 0.24 |
| Sucrose fatty acid ester | Initial | — | — | | 0.10 | 0.03 | | | | 0.02 | | 0.02 | | 0.02 | 0.19 |
| | 60° C. | Glass bottle (amber) | 2 W | 0.02 | 0.10 | 0.04 | 0.02 | | 0.02 | | | 0.02 | | 0.03 | 0.25 |
| | | Tightly closed | 1 M | 0.02 | 0.09 | 0.05 | 0.02 | 0.02 | 0.02 | | 0.02 | 0.02 | 0.02 | 0.02 | 0.30 |
| | 40° C./ 75% RH | Glass bottle (amber) Tightly closed | 1 M | 0.02 | 0.10 | 0.03 | 0.02 | 0.02 | | 0.02 | 0.02 | 0.02 | 0.02 | 0.02 | 0.29 |
| | | Glass bottle (amber) Open | 1 M | 0.02 | 0.09 | 0.03 | | 0.02 | | | 0.02 | 0.02 | 0.02 | 0.02 | 0.24 |
| Hydrogenated oil | Initial | — | — | | 0.10 | 0.02 | | | | 0.02 | 0.02 | 0.02 | 0.02 | 0.02 | 0.22 |
| | 60° C. | Glass bottle (amber) | 2 W | 0.02 | 0.10 | 0.03 | 0.02 | | | | 0.02 | 0.02 | | 0.03 | 0.24 |
| | | Tightly closed | 1 M | | 0.10 | 0.03 | 0.02 | 0.02 | | 0.02 | | 0.02 | 0.02 | 0.03 | 0.26 |
| | 40° C./ 75% RH | Glass bottle (amber) Tightly closed | 1 M | 0.02 | 0.10 | 0.03 | 0.02 | | | 0.02 | | 0.02 | | 0.02 | 0.23 |
| | | Glass bottle (amber) Open | 1 M | 0.02 | 0.09 | 0.03 | 0.02 | 0.02 | | 0.02 | 0.02 | | | 0.02 | 0.24 |

lations evaluated will determine the more promising approach identifying a drug product whose manufacturing process could be developed.

Objectives

To develop an immediate release oral solid dosage (OSD) form of MLS-101 using the following different approaches:

a) Direct Compression (DC), b) Roller compaction (RC), c) High Shear Wet Granulation (HSWG), To evaluate stability of dosage form developed.

Materials

The materials listed in Table 6 were used for this study. All materials were stored at room temperature (RT).

TABLE 6

| Materials | | | |
|---|---|---|---|
| Ingredient (Trade name) | Supplier | Function | Lot No. |
| MLS-101 (NA) | Mitsubishi Tanabe Pharma | API | 001 |
| Microcrystalline cellulose (MCC) type 102 (Tabulose 102) | Roquette (Formerly Blanver) | Filler | 1396 |
| Microcrystalline cellulose (MCC) type 101 (Tabulose 101) | Blanver | | 1162 |
| Lactose monohydrate 80 (Tabletose 80) | Meggle | | 1467 |
| Lactose monohydrate 312 (FastFlo 312) | Foremost | | 1331 |
| Mannitol 100SD (Pearlitol 100SD) | Roquette | | 1365 |
| Mannitol 400DC (Pearlitol 400DC) | Roquette | | 1171 |
| Dicalcium phosphate anhydrous (DCP) (Emcompress) | JRS Pharma | | 1447 |
| Croscarmellose sodium Type A (Solutab type A) | Roquette (Formerly Blanver) | Disintegrant | 1366 |
| Crospovidone XL (Polyplasdone XL) | ISP (Ashland) | | 1531 |
| Pregelatinized starch (Starch 1500) | Colorcon | | 1601 |
| Low substituted Hydroxypropyl cellulose (L-HPC, grade NBD-021) | ShinEtsu | | 7128042 |
| Colloidal silicone dioxide (Cab-O-Sil M5P) | Cabot | Glidant | 1521 |
| Copovidone S-630 (Plasdone S-630) | ISP (Ashland) | Binder | 1574 |
| Povidone type K-29/32 (Plasdone K-29/32) | | | 1459 |
| Magnesium stearate (Ligamed MF-2-V) | Peter Greven | Lubricant | 1212 |
| Talc (Luzenac Pharma M) | Imerys talc (formerly Rio Tinto Minerals) | | 1389 |
| Glyceryl dibehenate (Compritol 888 ATO) | Gattefossé | | 175284 |
| Stearic acid Type 50 (NA) | Spectrum | | 1627 |
| Opadry 85F18422 | Colorcon | Coating | 1529 |

Methods

Crystal State Evaluation

X-Ray Powder Diffraction—USP <941>:

The crystal state of the samples at different manufacturing steps was studied by X-Ray Powder Diffraction (XRPD), where applicable, using a Bruker X-ray diffractometer model D2 Phaser (Karlsruhe, Germany), with Cu Kα radiation ($\lambda$=1.54184 Å) at an increment of 0.01° 2θ with a 0.2 second step time (scan rate of 3° 2θ/min) over a range of 3-56° 2θ, a 0.6 mm divergence slit, 1.0 mm scattering plate, and 3.0 mm receiving window. Samples were analyzed using a low volume sample holder while the samples were kept under a constant rotation of 15 rpm during analysis.

Formulation Development Approaches

Table 7 presents the composition of direct compression (DC) formulations lots 1, 2A, 2C, 3A-5; roller compaction (RC) lot 2B; and high shear wet granulation (HSWG) lot 6. Table 8 presents the Placebo blends lots 7-10 (corresponding to the active lots 1, 4-6). Table 8 also contain the composition of 'new' (explanations below) DC formulations prototypes without excipients containing metallic ions lots 11, 13, and 15 with their respective Placebo lots 12, 14, and 16, respectively, and additional lots 17 to 19.

MLS-101 was discovered to be susceptible to salt disproportionation in the presence of excipients containing metallic salts. Thus, additional 'new' DC lots 11, 13, 15, 17, 18, and 19 (Table 8), without excipients such as dicalcium phosphate, croscarmellose sodium, and magnesium stearate were proposed to reduce the salt disproportionation risk.

The 100 mg FB tablet lot 19 was prepared as per lot 18 with MCC replaced by SMCC and with increased lubricant at 3%.

The blending of lots 1-5, 11, 13, 15, and 17-19 was performed using a GlobePharma MaxiBlend 4 qt V-blender model MB-I.

The Placebos were processed using a Patterson-Kelly BlendMaster 0.5 L V-blender. All placebo excipients (including Opadry) were de-lumped over a 600 μm sieve and blended for 3 min. The lubricant that was screened over the same sieve, added to the V-blender, and mixed for an additional 2 min.

TABLE 7

Composition of Different Formulations of MLS-101 Tablet Lots 1 to 6

| | Lot No. | | | | | | | | |
|---|---|---|---|---|---|---|---|---|---|
| | DC | | RC | | | | DC | | |
| | 1 12.5 mg API free base Tablet | | 2A | | 2B 25 mg API free base Tablet | | 2C | | 3A 100 mg API free base Tablet |
| | Batch Size: 600 g | | | | | | | | |
| Ingredient | % w/w | mg/ unit | % w/w | mg/ unit | % w/w | mg/ unit | % w/w | mg/ unit | % w/w |
| MLS-101 | 4.91 | 14.73 | 9.83 | 29.49 | 9.83 | 29.49 | 9.45 | 29.49 | 39.31 |
| MCC 102 | 32.09 | 96.27 | 45 | 135 | 45 | 135 | 43.27 | 135 | 18.69 |
| Lactose monohydrate 80 | 58 | 174 | | | | | | | |
| Mannitol 100SD | | | 40 | 120 | 40 | 120 | 38.46 | 120 | |
| DCP anhydrous | | | | | | | | | 37 |
| Copovidone S-630 | | | | | | | 3.85 | 12 | |
| MCC 101 | | | | | | | | | |
| Lactose monohydrate 312 | | | | | | | | | |
| Povidone K-29/32 | | | | | | | | | |
| Croscarmellose sodium | 4 | 12 | 4 | 12 | 4 | 12 | 3.85 | 12 | 4 |
| Magnesium stearate | 1 | 3 | 1.17 | 3.51 | 1.17 | 3.51 | 1.13 | 3.51 | 1 |
| Total | 100 | 300 | 100 | 300 | 100 | 300 | 100 | 312 | 100 |

| | Lot No. | | | | | | | | |
|---|---|---|---|---|---|---|---|---|---|
| | DC | | | | | | | HSWG | |
| | 3A 100 mg API free base Tablet | 3B | | 4 25 mg API free base Tablet | | 5 100 mg API free base Tablet | | 6 | |
| | Batch Size: 600 g | | | | | | | | |
| Ingredient | mg/ unit | % w/w | mg/ unit | % w/w | mg/ unit | % w/w | mg/ unit | % w/w | mg/ unit |
| MLS-101 | 117.93 | 37.80 | 117.93 | 9.07 | 29.48 | 36.28 | 117.91 | 36.28 | 117.91 |
| MCC 102 | 56.07 | 17.97 | 56.07 | 45.76 | 148.72 | 19.72 | 64.09 | | |
| Lactose monohydrate 80 | | | | | | | | | |
| Mannitol 100SD | | | | 40 | 130 | | | | |
| DCP anhydrous | 111 | 35.58 | 111 | | | 39 | 126.75 | | |
| Copovidone S-630 | | 3.85 | 12 | | | | | | |
| MCC 101 | | | | | | | | 18.72 | 60.84 |
| Lactose monohydrate 312 | | | | | | | | 37 | 120.25 |
| Povidone K-29/32 | | | | | | | | 3 | 9.75 |
| Croscarmellose sodium | 12 | 3.85 | 12 | 4 | 13 | 4 | 13 | 4 | 13 |
| Magnesium stearate | 3 | 0.96 | 3 | 1.17 | 3.80 | 1 | 3.25 | 1 | 3.25 |
| Total | 300 | 100 | 312 | 100 | 325 | 100 | 325 | 100 | 325 |

TABLE 8

Composition of Different Formulations of MLS-101 Tablet Lots 7 to 19

| | Lot No. | | | | | | | | | | | | | | | | | | |
|---|---|---|---|---|---|---|---|---|---|---|---|---|---|---|---|---|---|---|---|
| | Dry Blended Placebo | | | | | | | DC Tablet | | | | | | | | | | | |
| | 7 | 8 | 9 | 10 | 12 | 14 | 16 | 11 | | 13 | | 17 | | 18 | | 19 | | 15 | |
| | Placebo for lots 1, 4, 5, and 6, respectively | | | | Placebo for lots 11, 13/17/18, and 15, respectively | | | 12.5 mg API free base Tablet | | | | 25 mg API free base Tablet | | 100 mg API free base Tablet | | | | 12.5 mg API free base Tablet | |
| | | | | | | | | Batch Size: 600 g | | | | | | | | | | | |
| Ingredient | Batch Size: 150 g % w/w | | | | | | | % w/w | mg/ unit | % w/w | mg/ unit | % w/w | mg/ unit | % w/w | mg/ unit | % w/W | mg/ unit | % w/w | mg/ unit |
| MLS-101 | | | | | | | | 4.54 | 14.76 | 4.54 | 14.76 | 9.07 | 29.48 | 36.28 | 117.91 | 36.28 | 117.91 | 4.54 | 14.76 |
| MCC 102 | 35 | 49.83 | 38 | 36 | 33 | 31 | | 32.46 | 105.5 | 30.46 | 99 | 42.93 | 139.52 | 30.72 | 99.84 | | | | |
| SMCC HD 90 | | | | | | | | | | | | | | | | 30.72 | 99.84 | | |
| Lactose mono-hydrate 80 | 60 | | | | 60 | | | 56 | 182 | | | | | | | | | | |
| Mannitol 100SD | | 45 | | | | | | | | | | | | | | | | | |
| DCP anhydrous | | | 57 | | | | | | | | | | | | | | | | |
| Lactose mono-hydrate 312 | | | | 56 | | | | | | | | | | | | | | | |
| Croscarmellose sodium | 4 | 4 | 4 | 4 | | | | | | | | | | | | | | | |
| Povidone K-29/32 | | | | 3 | | | | | | | | | | | | | | | |
| Magnesium stearate | 1 | 1.17 | 1 | 1 | | | | | | | | | | | | | | | |
| Colloidal silicone dioxide | | | | | | 1 | 1 | | | 1 | 3.25 | 1 | 3.25 | 1 | 3.25 | 1 | 3.25 | 1 | 3.25 |
| Mannitol 400DC | | | | | | 60 | 92 | | | 56 | 182 | 39 | 126.75 | 24 | 78.0 | 23 | 74.75 | 87.46 | 284.25 |
| Crospovidone XL | | | | | 4 | | | 4 | 13 | | | | | | | | | | |
| Pregelatinized starch | | | | | | 6 | | | | 6 | 19.5 | 6 | 19.5 | 6 | 19.5 | 6 | 19.5 | | |
| Low substituted Hydroxypropyl cellulose | | | | | | | 5 | | | | | | | | | | | 5 | 16.25 |
| Talc | | | | | 3 | | | 3 | 9.75 | | | | | | | | | | |
| Glyceryl dibehenate | | | | | | 2 | | | | 2 | 6.5 | 2 | 6.5 | 2 | 6.5 | 3 | 9.75 | | |
| Stearic acid | | | | | | | 2 | | | | | | | | | | | 2 | 6.5 |
| Total | 100 | 100 | 100 | 100 | 100 | 100 | 100 | 100 | 325 | 100 | 325 | 100 | 325 | 100 | 325 | 100 | 325 | 100 | 325 |

Analytical Testing

The quality attributes of the drug product were assessed by analytical testing including appearance, content uniformity, assay, related substances, water content, and dissolution profile.

Stability Program

The first R&D stability study was performed on 12.5 mg MLS-101 FCT lot 1, 25 mg FCT lot 4, and 100 mg FCT lots 5 and 6.

A second R&D stability study was performed on 12.5 mg MLS-101 FCT lots 11, 13, and 15.

A third R&D stability study was performed on 25 mg and 100 mg MLS-101 FCT lots 17 and 18, respectively.

The tablets were packaged in Aclar® blister with 10 FCT per blister. The blister material Pentapharm Aclar PA 160/02 (254/15, Clear, 160 mm width, Color #: 71/9400, Klöckner lot 0075966400) and the foil was a 25 μm Aluminium lidding push through (Constancia AL109CSM.

A small portion of the tablets were also packaged in 60 cc round white opaque high-density polyethylene (HDPE) bottles (Drug Plastics & Glass Co.), without caps (so-called 'open') to induce worst-case stability conditions.

The Placebo blends were packaged in 60 cc round white opaque HDPE bottles (Drug Plastics & Glass Co.) with induction sealed child resistant polypropylene caps (Berry).

The stability prototypes were incubated under ICH recommendation for intermediate (30° C./65% RH), long-term (25° C./60% RH), and accelerated (40° C./75% RH) stability conditions. Extra samples were incubated at 5° C. for reference. The blisters and open bottles were placed in 24/7 monitored chambers as per stability protocols presented in Table 9, Table 10, and Table 11.

TABLE 9

Stability protocol for MLS-101 tablet lots 1 (12.5 mg FCT), 4 (25 mg FCT), 5-6 (100 mg FCT), and matching Placebo blends.

| | | Temperature/Relative Humidity | | | | | | | | | |
|---|---|---|---|---|---|---|---|---|---|---|---|
| Lot No. | | 30° C./65% | 25° C./ | 40° C./ | Timepoints (months) | | | | | | |
| (Strength) | Packaging | RH | 60% RH | 75% RH | 0 | 1 | 2 | 3 | 6 | 9 | 12 |
| 1 (12.5 mg FCT); | Aclar | Y | N/A | N/A | X | Y | Y | Y | Y | N/A | N/A |
| 4 (25 mg FCT); | Blisters | N/A | X Y | N/A | | Y | Y | X | X | X | X |
| 5 (100 mg FCT); | | N/A | N/A | X | | X | X | X | X | N/A | N/A |
| 6 (100 mg FCT) | | | | | | | | | | | |
| 7 (Placebo Blend for | 40 g Blend in | Y | N/A | N/A | | Y | Y | Y | Y | N/A | NA |
| lot 1); | 60 cc HDPE | N/A | X Y | N/A | | Y | Y | X | X | X | X |
| 8 (Placebo Blend for | Bottle with | N/A | N/A | X | | X | X | X | X | N/A | N/A |
| lot 4); | Induction | | | | | | | | | | |
| 9 (Placebo Blend for | Sealed CRC | | | | | | | | | | |
| lot 5); | PP Caps | | | | | | | | | | |
| 10 (Placebo Blend for lot 6) | | | | | | | | | | | |

| | | Temperature/Relative Humidity | | | | | | | | | |
|---|---|---|---|---|---|---|---|---|---|---|---|
| | | 30°C/65% | 25°C/ | 40°C/ | Timepoints (Weeks) | | | | | | |
| Lot # (Strength) | Packaging | RH | 60% RH | 75% RH | 0 | 0.5-mo | 7 weeks | 11 weeks | 24 weeks | N/A | N/A |
| 1 (12.5 mg FCT); | 60 cc HDPE | N/A | N/A | N/A | X | N/A | N/A | N/A | N/A | N/A | N/A |
| 4 (25 mg FCT); | Bottle/Open | N/A | N/A | N/A | | N/A | N/A | N/A | N/A | N/A | N/A |
| 5 (100 mg FCT); | caps | N/A | N/A | Z | | Z | Z | Z | Z | N/A | N/A |
| 6 (100 mg FCT) | | | | | | | | | | | |

Sample to be analyzed for:
X: Samples to be analyzed for appearance, assay, related substances, water content and dissolution; CU T = 0 only.
Y: Samples will be removed from chamber and analyzed.
Z: Samples will be removed from chamber and analyzed.

TABLE 10

Stability protocol for MLS-101 12.5 mg FCT lots 11, 13, 15, and matching Placebo blends.

| | | Temperature/Relative Humidity | | | | | | | | | |
|---|---|---|---|---|---|---|---|---|---|---|---|
| | | 30° C./65% | 25° C./ | 40° C./ | Timepoints (months) | | | | | | |
| Lot No. (Strength) | Packaging | RH | 60% RH | 75% RH | 0 | 1 | 2 | 3 | 6 | 9 | 12 |
| 11 (12.5 mg FCT); | Aclar Blisters | Y | N/A | N/A | X | Y | Y | Y | Y | N/A | N/A |
| 13 (12.5 mg FCT); | | N/A | X Y | N/A | | Y | Y | X | X | X | X |
| 15 (12.5 mg FCT); | | N/A | N/A | X | | X | X | X | X | N/A | N/A |
| 12 (Placebo Blend for | 40 g Blend in | Y | N/A | N/A | | Y | Y | Y | Y | N/A | NA |
| lot 11); | 60 cc HDPE | N/A | X Y | N/A | | Y | Y | X | X | X | X |
| 14 (Placebo Blend for | Bottle with | N/A | N/A | X | | X | X | X | X | N/A | N/A |
| lot 13); | Induction | | | | | | | | | | |
| 16 (Placebo Blend for | Sealed CRC PP | | | | | | | | | | |
| lot 15) | Caps | | | | | | | | | | |

| | | Temperature/Relative Humidity | | | | | | | | | |
|---|---|---|---|---|---|---|---|---|---|---|---|
| | | 30° C./65% | 25°C/ | 40°C/ | Timepoints (months) | | | | | | |
| Lot # (Strength) | Packaging | RH | 60% RH | 75% RH | 0 | 0.5-mo | 1 | 2 | 3 | N/A | N/A |
| 11 (12.5 mg FCT); | 60 cc HDPE | N/A | N/A | N/A | X | N/A | N/A | N/A | N/A | N/A | N/A |
| 13 (12.5 mg FCT); | Bottle/Open | N/A | N/A | N/A | | N/A | N/A | N/A | N/A | N/A | N/A |
| 15 (12.5 mg FCT); | caps | N/A | N/A | Z | | Z | Z | Z | Z | N/A | N/A |

Sample to be analyzed for:
X: Samples to be analyzed for appearance, assay, related substances, water content and dissolution; CU T = 0 only.
Y: Samples will be removed from chamber and analyzed.
Z: Samples will be removed from chamber and analyzed.

TABLE 11

Stability protocol for MLS-101 25 mg FCT lot 17 and 100 mg FCT lot 18.

| | | Temperature/Relative Humidity | | | | | | | | | |
|---|---|---|---|---|---|---|---|---|---|---|---|
| | | 30° C./65% | 25° C./ | 40° C./ | Timepoints (months) | | | | | | |
| Lot # (Strength) | Packaging | RH | 60% RH | 75% RH | 0 | 1 | 2 | 3 | 6 | 9 | 12 |
| 17 (25 mg FCT); | Aclar listers | Y | N/A | N/A | X | Y | Y | Y | Y | N/A | N/A |
| 18 (100 mg FCT); | | N/A | X Y | N/A | | Y | Y | X | X | X | X |
| | | N/A | N/A | X | | X | X | X | X | N/A | N/A |
| | | Temperature/Relative Humidity | | | | | | | | | |
| | | 30° C./65% | 25° C./ | 40° C./ | Timepoints (months) | | | | | | |
| Lot # (Strength) | Packaging | RH | 60% RH | 75% RH | 0 | 0.5-mo | 1 | 2 | 3 | N/A | N/A |
| 17 (25 mg FCT); | 60 cc HDPE | N/A | N/A | N/A | X | N/A | N/A | N/A | N/A | N/A | N/A |
| 18 (100 mg FCT); | Bottle/Open | N/A | N/A | N/A | | N/A | N/A | N/A | N/A | N/A | N/A |
| | caps | N/A | N/A | Z | | Z | Z | Z | Z | N/A | N/A |

Sample to be analyzed for:
X: Samples to be analyzed for appearance, assay, related substances, water content and dissolution; CU T = 0 only.
Y: Samples will be removed from chamber and analyzed.
Z: Samples will be removed from chamber and analyzed.

Formulation Development

Crystal State Evaluation Results

The DC lots 1, 4, and 5 (FIG. 5, FIG. 6, FIG. 7, respectively) as well as HSWG lot 6 (FIG. 8) (prepared with metal salts containing excipients) each showed a different XRP diffractogram for the final blends (due to the different excipients used in each formulation) and presented crystalline characteristic peaks as expected. The uncoated tablet XRPD showed less intensity for all lots when compared to those from their respective final blend but without any other noticeable change. For lot 6, samples from various manufacturing steps presented similar XRPD pattern to that of the final blend.

For the new DC lots 11, 13, and 15 (FIG. 9, FIG. 10, and FIG. 11, respectively) prepared without metal salts containing excipients, the XRPD pattern were also different from each other. Contrary to the previous lots, the uncoated tablets showed higher intensity crystalline peaks than those of their respective final blend. There were no major changes observed for the XRPD pattern for the film coated tablet when compared to that of its corresponding uncoated tablet.

For the DC lots 17 and 18 (FIG. 12 and FIG. 13, respectively) prepared with same excipients as per lot 13 but at ca. 9 and 36% drug load respectively, the XRPD patterns were in general similar to those of lot 13 with regard to final blend up to uncoated tablet Trial #2 samples (medium or high compression force). However, the XRPD pattern for lot 18 (prepared at high drug load) presented noticeable reduced intensity of crystalline peaks for tablet from Trial #3 compressed at the maximum compression force. Again, there were no major changes observed for the XRPD pattern for the film coated tablet when compared to that of its corresponding uncoated tablet.

Analytical Testing

Initial analytical results for appearance, assay, degradation products, and dissolution of FCT lots 1 and 4-6 can be found in FIG. 14 and FIG. 15. The drug products presented an assay comprised between 97-100% and no impurities ≥0.05%. However, low dissolution in water was noted with 55, 72, 73, and 86% released, respectively for lots 1, 4, 5, and 6 within the first 30 minutes. In comparison, the dissolution profiles in 0.1N HCl showed a release of 96, 94, 90, and 93% for the same lots respectively within the same 30 minutes.

Further investigations were then carried out using Swedish orange capsule size '0' lots 1A (capsule filled with API only) and 1B (final uncompressed blend from lot 1). The results showed fast dissolution in water with 104% released for capsule lot 1A (with API only) within 15 minutes when compared again to low recovery ca. 33% for capsule lot 1B (final blend lot 1) within 30 minutes. It was hypothesized that the metallic ion containing excipients (i.e., dicalcium phosphate, croscarmellose sodium, and magnesium stearate) used in the prototypes evaluated may have induced salt disproportionation thus producing the API free base that is poorly soluble in water. This hypothesis was revealed as a potential risk which lead to the second round of prototyping as explained previously.

The results for new formulation without metallic ion excipients for appearance, assay, degradation products, dissolution, and content uniformity of FCT lots 11, 13, and 15 (all 12.5 mg MLS-101 free base) can be found in FIG. 16, FIG. 17, and FIG. 18. All drug products presented no impurities ≥0.05%. Lots 11 and 13 presented similar assay results. Faster dissolution with 98 and 96% released in water and in 0.1N HCl, respectively, within 15 minutes was noted for lot 13 while ca. 87% was released in both media for lot 11 within 15 minutes. Content uniformity results of 98 and 96% LC were obtained for lots 11 and 13, respectively. On the other hand, Lot 15 prepared with Mannitol contains API in an amount of 88.5%, therefore, Lot 15 presented a low assay of 88.5%, lower dissolution profiles with 92 and 89% released in water and 0.1N HCl, respectively, within 15 minutes and, low content uniformity of 89.6% LC.

Conclusion

The final lubricated blend of DC formulation lot 5 prepared at high drug load (36.28%) with microcrystalline cellulose and dicalcium phosphate presented the lowest bulk density of 0.38 g/cm3 and showed 'passable' flow. The highest bulk density of 0.64 g/cm3 was obtained for DC lot 15 prepared at low drug load (4.54%) with mannitol 400DC and showed 'good' flow. All other DC formulations (without regard to the drug load) lots 1, 4, 11, and 13 as well as HSWG lot 6 presented a bulk density ranging from 0.41-0.58 g/cm3 and showed 'fair' flow.

Most formulations produced tablets that met target weight with an RSD <1.8% (except lot 3A with RSD 3.7%), and friability <0.5%. In general, DC formulation tablets compressed at high compression or intermediate force did not show capping, lamination, picking nor sticking except lot 11 (prepared with talc and without colloidal silicon dioxide). Tablets compressed at low compression force revealed that a thin film of powder adhered on punches or even minor picking when chrome tipped punches were used.

The disintegration time (DT) for DC formulations was less than 2 min while that of the HSWG lot 6 was less than 7 minutes. The DT was well within the target ≤15 min that is generally accepted for immediate release oral solid dosage forms.

The initial analytical results for lots 1, 4-6 revealed a potential issue with regards to salt disproportionation. It was hypothesized that the metallic ion containing excipients (i.e., dicalcium phosphate, croscarmellose sodium, and magnesium stearate) used in the prototypes evaluated may have induced salt disproportionation thus producing the API free base that is poorly soluble in water. This hypothesis was confirmed as a potential risk which led to the second round of prototyping.

Thus newer lots 11, 13, and 15 formulated with Microcrystalline cellulose and/or Mannitol as fillers; with Crospovidone XL, Pregelatinized starch, and Low substituted Hydroxypropyl cellulose as disintegrant; and with Talc, Glyceryl dibehenate, and Stearic acid as lubricant, presented encouraging data for assay, degradation product, dissolution (in both water and 0.1N HCL). Lots 11 and 13 also presented encouraging data for content uniformity. Specifically, the formulations demonstrated <10% disproportionation as demonstrated by the formulations' dissolution profile and XRPD.

The results indicate that the DC formulation lot 13 appeared to be promising. Thus, a 25 mg and a 100 mg coated tablet are prepared with excipients comprising microcrystalline cellulose 102, mannitol 400DC, pregelatinized starch, and glyceryl dibehenate.

What is claimed is:

1. A pharmaceutical composition comprising a halogen anion salt of a compound having the formula:

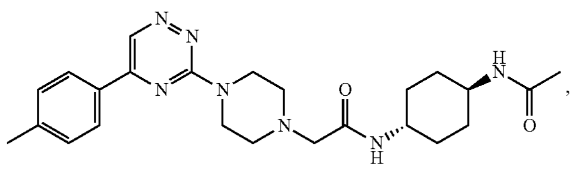

3-[4-[[trans-4-(acetoamino)cyclohexyl]carbamoylmethyl]piperazin-1-yl]-5-(p-tolyl)-1,2,4-triazine and one or more excipients, wherein the one or more excipients do not comprise a metal salt, and wherein the pharmaceutical composition avoids inducing disproportionation of the halogen anion salt of the compound.

2. A pharmaceutical composition comprising a halogen anion salt of a compound having the formula:

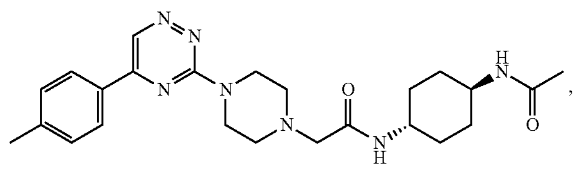

3-[4-[[trans-4-(acetoamino)cyclohexyl]carbamoylmethyl]piperazin-1-yl]-5-(p-tolyl)-1,2,4-triazine and one or more excipients, wherein the one or more excipients do not comprise a metal salt, and wherein the pharmaceutical composition has a dissolution profile such that more than 70% of the compound is dissolved in 15 minutes in an in vitro dissolution test of the pharmaceutical composition using USP Apparatus 2 Paddle Method at 50 rpm in a dissolution medium of water at 37° C.

3. The pharmaceutical composition of claim 1, wherein the salt of the compound is an HBr salt.

4. The pharmaceutical composition of claim 2, wherein the salt of the compound is an HBr salt.

5. The pharmaceutical composition of claim 2, wherein the salt of the compound is in crystalline form.

6. The pharmaceutical composition of claim 2, wherein the salt of the compound is in amorphous form.

7. The pharmaceutical composition of claim 2, comprising 5 milligrams to 150 milligrams of the compound.

8. The pharmaceutical composition of claim 7, wherein the pharmaceutical composition comprises:

a) about 30 wt % to about 60 wt % of lactose, mannitol, or a combination thereof;
b) about 25 wt % to about 50 wt % of microcrystalline cellulose;
c) about 1 wt % to about 10 wt % of polyvinylpyrrolidone, pregelatinized starch, or a combination thereof; and
d) about 1 wt % to about 10 wt % of talc, glyceryl dibehenate, colloidal silicone dioxide, or a combination of two or more thereof.

9. The pharmaceutical composition of claim 7, wherein the compound is more soluble in water than the same compound in an equivalent pharmaceutical composition comprising a calcium salt, a sodium salt or magnesium salt, wherein the pharmaceutical composition avoids disproportionation in excess of 10% when stored at 25° C. and 60% relative humidity for 6 months in a closed container.

10. The pharmaceutical composition of claim 2, wherein the pharmaceutical composition comprises about 5 milligrams to about 20 milligrams of the compound.

11. The pharmaceutical composition of claim 10, wherein the pharmaceutical composition comprises:

a) about 1 wt % to about 8 wt % of the compound;
b) about 50 wt % to about 60 wt % of lactose, mannitol, or a combination thereof;
c) about 25 wt % to about 40 wt % of microcrystalline cellulose;
d) about 1 wt % to about 10 wt % of polyvinylpyrrolidone, pregelatinized starch, or a combination thereof; and
e) about 1 wt % to about 10 wt % of talc, glyceryl dibehenate, colloidal silicone dioxide, or a combination of two or more thereof.

12. The pharmaceutical composition of claim 2, wherein the pharmaceutical composition comprises about 15 milligrams to about 35 milligrams of the compound.

13. The pharmaceutical composition of claim 12 wherein the pharmaceutical composition comprises:

a) about 5 wt % to about 15 wt % of the compound;
b) about 30 wt % to about 50 wt % of mannitol;
c) about 30 wt % to about 50 wt % of microcrystalline cellulose;
d) about 1 wt % to about 10 wt % of pregelatinized starch; and
e) about 1 wt % to about 5 wt % of glyceryl dibehenate, colloidal silicone dioxide, or a combination thereof.

14. The pharmaceutical composition of claim 2, wherein the pharmaceutical composition comprises about 80 milligrams to about 120 grams of the compound.

15. The pharmaceutical composition of claim 14, wherein the pharmaceutical composition comprises:
a) about 30 wt % to about 40 wt % of the compound;
b) about 20 wt % to about 30 wt % of mannitol;
c) about 20 wt % to about 40 wt % of microcrystalline cellulose;
d) about 1 wt % to about 10 wt % of pregelatinized starch;
e) about 1 wt % to about 5 wt % of glyceryl dibehenate, colloidal silicone dioxide, or a combination thereof.

16. The pharmaceutical composition of claim 2, wherein the pharmaceutical composition is a tablet.

17. A process for making a pharmaceutical composition comprising a halogen anion salt of a compound having the formula:

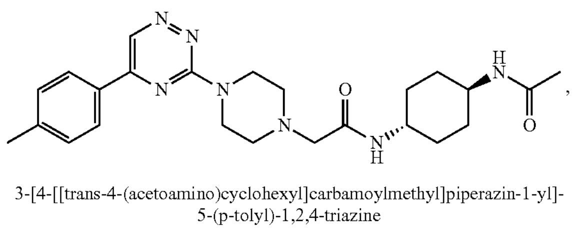 [SMILES: CC(=O)N[C@H]1CC[C@H](NC(=O)CN2CCN(c3nncc(-c4ccc(C)cc4)n3)CC2)CC1]

3-[4-[[trans-4-(acetoamino)cyclohexyl]carbamoylmethyl]piperazin-1-yl]-5-(p-tolyl)-1,2,4-triazine and one or more excipients, wherein the one or more excipients do not comprise a metal salt, wherein the pharmaceutical composition avoids inducing disproportionation of the halogen anion salt of the compound and/or the pharmaceutical composition has a dissolution profile such that more than 70% of the compound is dissolved in 15 minutes in an in vitro dissolution test of the pharmaceutical composition using USP Apparatus 2 Paddle Method at 50 rpm in a dissolution medium of water at 37° C., comprising:
a) obtaining a halogen anion salt of a compound having the formula:

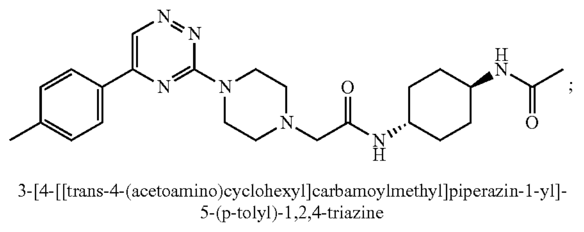 [SMILES: CC(=O)N[C@H]1CC[C@H](NC(=O)CN2CCN(c3nncc(-c4ccc(C)cc4)n3)CC2)CC1]

3-[4-[[trans-4-(acetoamino)cyclohexyl]carbamoylmethyl]piperazin-1-yl]-5-(p-tolyl)-1,2,4-triazine and
b) mixing the salt with the one or more excipients to thereby produce the pharmaceutical composition.

18. The process of claim 17, wherein step b) comprises:
i) blending the salt with one or more excipients; and
ii) roller compaction of the product of step i); and
iii) milling the product of step ii);
wherein the one more excipients of step i) comprises stearic acid; and wherein step b) further comprises a step of blending the product of step iii) with one or more additional excipients, wherein the one or more additional excipients comprise stearic acid.

19. The process of claim 17, wherein the one or more excipients are selected from the group consisting of microcrystalline cellulose, lactose, mannitol, polyvinylpyrrolidone, colloidal silicone dioxide, pregelatinized starch, low-substituted hydroxypropyl cellulose, talc, glyceryl dibehenate, and stearic acid.

20. A method of treating hypertension and/or reducing blood pressure in a hypertensive subject, the method comprising administering to the hypertensive subject the composition of claim 2.

21. A method of inhibiting CYP11β2 beta hydroxylase in a subject, the method comprising administering to the subject the composition of claim 2.

* * * * *